US012690900B2

(12) United States Patent
Lim et al.

(10) Patent No.: US 12,690,900 B2
(45) Date of Patent: Jul. 28, 2026

(54) SURGICAL INSTRUMENT AND METHOD

(71) Applicant: Warsaw Orthopedic, Inc., Warsaw, IN (US)

(72) Inventors: Roy K. Lim, Germantown, TN (US); Mark C. Dace, Memphis, TN (US); Richard Q Brown, Memphis, TN (US); Adam D Glaser, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 89 days.

(21) Appl. No.: 18/519,625

(22) Filed: Nov. 27, 2023

(65) Prior Publication Data

US 2025/0169860 A1      May 29, 2025

(51) Int. Cl.
*A61B 17/70*          (2006.01)

(52) U.S. Cl.
CPC ........ *A61B 17/7077* (2013.01); *A61B 17/708* (2013.01)

(58) Field of Classification Search
CPC .................................... A61B 17/7077–17/708
See application file for complete search history.

(56) References Cited

U.S. PATENT DOCUMENTS

| | | | |
|---|---|---|---|
| 8,894,648 B2 * | 11/2014 | Dominik | A61B 17/7077 606/57 |
| 10,751,127 B2 | 8/2020 | Dace et al. | |
| 2007/0213716 A1 | 9/2007 | Lenke et al. | |
| 2011/0106082 A1 * | 5/2011 | Kave | A61B 17/708 606/86 A |
| 2014/0039556 A1 * | 2/2014 | Rutschmann | A61B 17/7002 606/266 |
| 2015/0320458 A1 * | 11/2015 | Rezach | A61B 17/7085 606/279 |
| 2016/0262810 A1 * | 9/2016 | Meyer | A61B 17/7049 |
| 2017/0156814 A1 * | 6/2017 | Thommen | A61B 5/24 |
| 2018/0070994 A1 * | 3/2018 | Leff | A61B 17/7079 |
| 2019/0216454 A1 * | 7/2019 | Thommen | A61B 90/57 |
| 2019/0307492 A1 | 10/2019 | Chao et al. | |
| 2020/0179008 A1 * | 6/2020 | Biedermann | A61B 17/7001 |
| 2020/0237410 A1 * | 7/2020 | Gabos | A61B 17/7079 |

FOREIGN PATENT DOCUMENTS

WO          2019058344 A1      3/2019

OTHER PUBLICATIONS

International Search Report. International Application No. PCT/IB2024/061822. Dated Feb. 20, 2025. 4pgs.

* cited by examiner

*Primary Examiner* — Julianna N Harvey
(74) *Attorney, Agent, or Firm* — Sorell, Lenna & Schmidt, LLP

(57)          ABSTRACT

A surgical instrument comprises a first member including at least a portion of a first spheroidal joint and a first lock engageable with a first bone element fixed with a first vertebrae. A second member includes at least a portion of a second spheroidal joint and a second lock engageable with a second bone element fixed with a second vertebrae. A linkage is simultaneously engageable with the spheroidal joints to lock the second member relative to the first member fixed with the first vertebrae. Surgical systems and methods are disclosed.

15 Claims, 29 Drawing Sheets

SURGICAL INSTRUMENT AND METHOD

TECHNICAL FIELD

The present disclosure generally relates to medical devices for the treatment of musculoskeletal disorders, and more particularly to a surgical system, surgical instruments and methods for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes pediatric treatment, deformity procedures, correction, fusion, fixation, discectomy, laminectomy, corpectomy and implantable prosthetics. As part of these surgical treatments, spinal implants, for example, bone fasteners, spinal rods and interbody devices can be used to provide stability to a treated region. Surgical instruments can be employed to prepare tissue surfaces and immobilize vertebrae via bone mounting devices. Surgical treatment may also employ surgical instruments to deliver and manipulate implants for engagement with vertebrae to position and align one or more vertebrae. This disclosure describes an improvement over these prior technologies.

SUMMARY

In one embodiment, a method for treating a spine is provided. The method comprises the steps of: registering a plurality of vertebrae including at least a first vertebra and a second vertebra; fixing a first bone element with the first vertebra; fixing a second bone element with the second vertebra; engaging a first lock of a surgical instrument with the first bone element in a locking orientation, the surgical instrument including a first member having at least a portion of a first spheroidal joint and the first lock, the surgical instrument further including a second member including at least a portion of a second spheroidal joint and a second lock, and a linkage; engaging the second lock with the second bone element in a locking orientation; and simultaneously engaging the spheroidal joints to lock the second member relative to the first member. In some embodiments, surgical systems, instruments, constructs and implants are disclosed.

In one embodiment, the method includes registering a plurality of vertebrae including at least a first vertebra, a second vertebra, a third vertebra, a fourth vertebra, a fifth vertebra and a sixth vertebra; manually fixing a first bone pin with the first vertebra; fixing a second bone pin with the second vertebra via robotic guidance; engaging a first lock of a surgical instrument with the first bone pin in a locking orientation, the surgical instrument including a first arm having at least a portion of a first spheroidal joint and the first lock, the surgical instrument further including a second arm including at least a portion of a second spheroidal joint and a second lock, and a linkage; engaging the second lock with the second bone pin in a locking orientation; simultaneously engaging the spheroidal joints to lock the second arm relative to the first arm; and fixing a first bone fastener with a third vertebra disposed between the first vertebra and the second vertebra.

In one embodiment, a surgical instrument is provided. The surgical instrument includes a first member including at least a portion of a first spheroidal joint and a first lock engageable with a first bone element fixed with a first vertebra. A second member includes at least a portion of a second spheroidal joint and a second lock engageable with a second bone element fixed with a second vertebra. A linkage is simultaneously engageable with the spheroidal joints to lock the second member relative to the first member fixed with the first vertebrae.

BRIEF DESCRIPTION OF THE DRAWINGS

The present disclosure will become more readily apparent from the specific description accompanied by the following drawings, in which.

DETAILED DESCRIPTION

Figure 1:
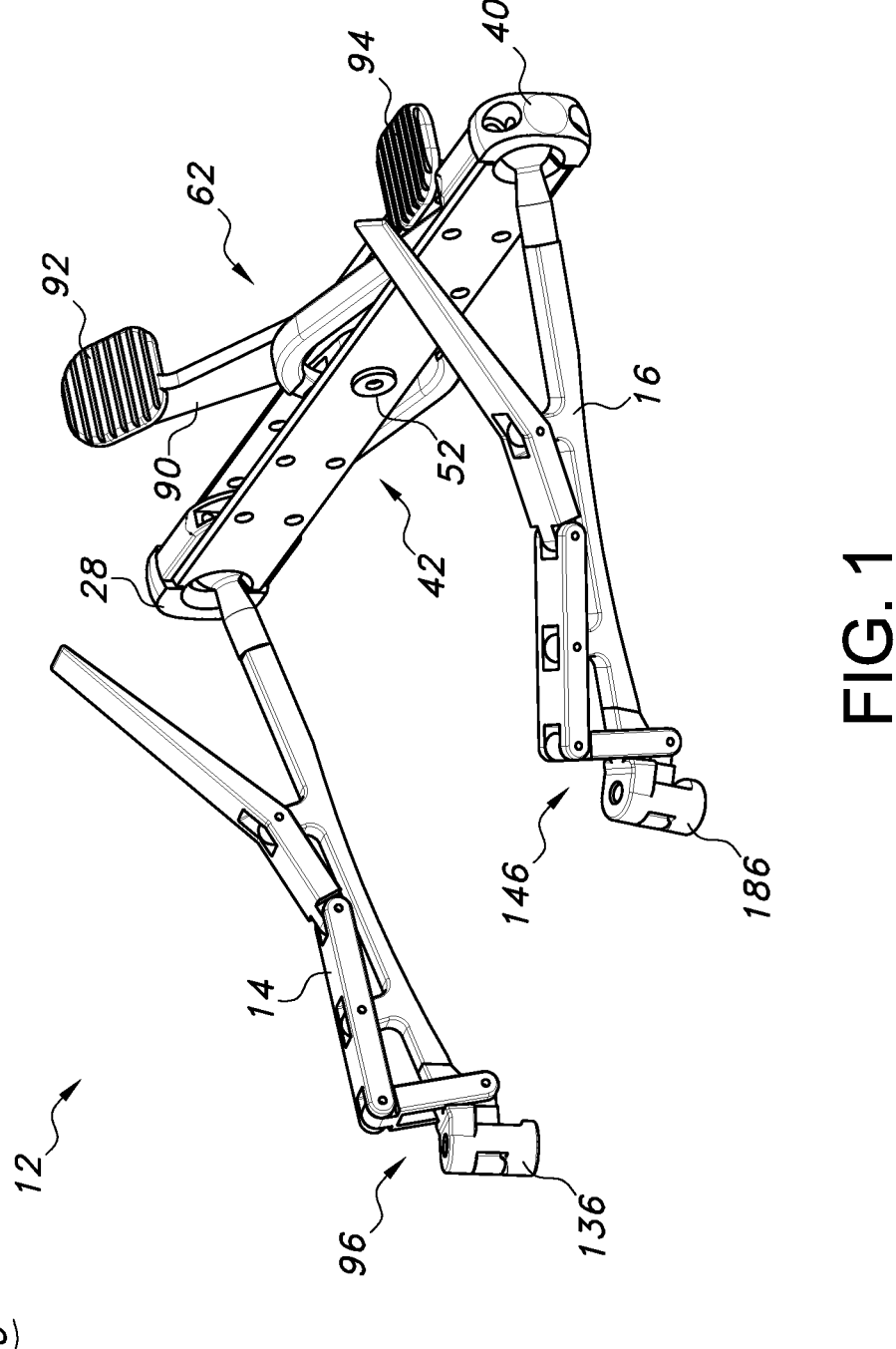
FIG. 1 is a perspective view of components of one embodiment of a surgical system in accordance with the principles of the present disclosure.

The exemplary embodiments of the surgical system and related methods of use disclosed are discussed in terms of medical devices, implants and surgical instruments for the treatment of musculoskeletal disorders and more particularly, in terms of a surgical system including a surgical instrument and related components for accessing a spine to facilitate treatment thereof and a method for treating a spine. In some embodiments, the present surgical system includes a surgical instrument having lockable features that facilitate immobilizing vertebrae via bone mounting. In some embodiments, the surgical instrument is configured to connect a first vertebral segment to a second vertebral segment to stabilize the vertebral segments and adjacent vertebral segments for improved rigidity relative to an unconnected or singularly stabilized vertebral segment. In some embodiments, the surgical instrument includes one or more locks to fix the first vertebral segment relative to the second vertebral segment. In some embodiments, the surgical instrument includes lockable linkages and arms having poly axial movement that connect with bone mounting components to immobilize selected vertebrae. In some embodiments, the present surgical system can be employed with surgical navigation and/or robotics. In some embodiments, the present surgical system can be employed with surgical procedures including pediatric spine treatment and/or deformity correction. In some embodiments, the surgical systems and methods of the present disclosure are employed with a spinal treatment, for example, relating to a cervical, thoracic, lumbar and/or sacral region of a spine.

In some embodiments, the present surgical system includes a surgical instrument having a linkage connected with a first spheroidal joint that supports a first arm for relative poly axial movement. The first arm is lockable with a bone mounting element fixed with a first vertebral surface. The linkage is connected with a second spheroidal joint that supports a second arm for relative poly axial movement. The second arm is lockable with a bone mounting element fixed with a second vertebral surface. The linkage is simultaneously engageable with the spheroidal joints to lock the second arm relative to the first arm fixed with the first vertebral surface. In some embodiments, the present surgical instrument advantageously improves modularity and ease of interconnection and attachment of instrument components with surgical apparatus, surgical navigation, robotics and/or vertebrae. In some embodiments, the present surgical instrument advantageously facilitates attachment to one or more bone mounting elements to various locations with vertebrae such as an articular facet, a pedicle, a lamina and/or a vertebral body. In some embodiments, the present surgical instrument advantageously facilitates attachment of one or more bone mounting elements to various locations with vertebral surfaces such as vertebrae, including an articular facet, a pedicle, a lamina and/or a vertebral body, and/or adjacent tissue and joints. In some embodiments, the present surgical instrument advantageously facilitates attachment of one or more bone mounting elements to vertebral, sacral and/or iliac regions as described herein.

In some embodiments, the present surgical system includes a surgical instrument, for example, a surgical mount, including a first spheroidal joint and a second spheroidal joint, each including a spherical part and a socket that are connectable to an over-center linkage. In some embodiments, the surgical mount includes a frame and a first arm and a second arm that are connected to the frame. In some embodiments the arms each include the spherical part of the spheroidal joint. In some embodiments, the linkage and each of the spheroidal joints are configured to selectively lock and unlock the arms of the surgical mount relative to the frame. In some embodiments, the linkage is configured to lock the spheroidal joints via a selected locking force. In some embodiments, the linkage includes a first curved link and a second curved link, and a lever including a first handle and a second handle. In some embodiments, the linkage fixes the arms in a locked position and an unlocked position. In the unlocked position, the arms are selectively movable relative to the frame. In some embodiments, in the unlocked position, the spherical part of the arm is captured within a portion of the joint including the socket. In some embodiments, in the unlocked position, clearance exists between the spherical part and the socket for arm movement. In some embodiments, in the unlocked position, the spherical parts have freedom to articulate relative to the locked linkage. In some embodiments, the lever can be toggled such that both the spherical part and the socket engage for locking.

In some embodiments, the surgical instrument includes a linkage having a first link and a second link. In some embodiments, a portion of the linkage is curved at an end. In some embodiments, the links adjust a force needed to move the linkage to an over-center position and allows for adjustable clamping force on the joint. In some embodiments, the surgical instrument includes a first end cap and a second end cap. In some embodiments, each of the end caps include a socket. In some embodiments, the linkage includes a centrally disposed linkage disposable in a locked and unlocked position. In some embodiments, a lever is depressed to close clearance between each spherical part and socket. In some embodiments, the lever includes an over-center lever that is configured to maintain the surgical instrument in the locked and/or unlocked position. In some embodiments, force is applied to the lever to elastically deform and lengthen the linkages. In some embodiments, the linkage is positioned over-center relative to the links and is locked into a closed position. In some embodiments, the over-center mechanism maintains the locking and unlocking of the arms for ease of use. In some embodiments, the linkage can be calibrated for variable force that is applied to the spheroidal joints.

In some embodiments, the arms each include a lock disposed at a distal end. In some embodiments, each lock includes an over-center linkage and a plate. In some embodiments, the plate is configured to capture a bone element, for example, a pin. In some embodiments, the plate is movable relative to the linkage. In some embodiments, the plate is configured to rotate, for example, tilt to engage the pin. In some embodiments, the lock is oriented in a locked and an unlocked position. In some embodiments, in the unlocked position, the pin translates freely through an engagement receptacle disposed at the distal end of the arm. In some embodiments, the plate is disposed perpendicular relative to a through hole of the engagement receptacle to facilitate freedom of translation of the pin. In some embodiments, the linkage includes an over-center lever. In some embodiments, when depressed, the lever is configured to translate the plate into a selected orientation to engage the pin in the locked position, preventing pin translation. In some embodiments, the plate is oriented in a tilted position to capture the pin. In some embodiments, the lever is depressed to place the pin in the unlocked position, disengaging the plate from the pin. In some embodiments, the lever facilitates perpendicular positioning of the plate relative to the engagement receptacle.

In some embodiments, the present surgical system includes a surgical instrument that advantageously improves registration ability and spinal stability. In some embodiments, one or more components of the present surgical system avoids one or more drawbacks associated with mounting a robot to a patient before registration during a robotic assisted procedure, for example, to immobilize a patient's vertebral body/bodies relative to the robotic system. In some embodiments, one or more components of the present surgical system avoids one or more drawbacks associated with operating on more than two vertebral levels above and below a surgical mount, for example, to avoid excessive motion of selected spinal segments during a robotic assisted procedure. In some embodiments, one or more components of the present surgical system avoids one or more drawbacks associated with positioning a surgical mount during image registration, for example, to avoid motion and enable the maximum number of spinal levels within a single registration. In some embodiments, one or more components of the present surgical system avoids interference of a surgical mount during registration, for example, drawbacks associated with radiopacity of surgical mounts which can lead to inaccuracy such as registration failure.

In some embodiments, the present surgical system includes a surgical instrument that advantageously improves registration ability by attaching a robot to patient bone, for example, vertebrae, and registering levels above an initial surgical mount to avoid surgical mount interference with registration. In some embodiments, once registered, the surgeon can drive a pin into a spinal segment via robotic guidance, for example, at two vertebral levels above the robot/surgical mount level, and then attach the pin to the robot/surgical mount level via the present surgical mount that includes a low force mount. In some embodiments, the present surgical system extends the allowable levels for robotic operation and allows a surgeon to operate at two vertebral levels above the pin, for example, at four vertebral levels above the initial position of the robot/surgical mount. In some embodiments, the present surgical mount is configured for driving a pin into a vertebra for linking selected vertebral levels. In some embodiments, the surgical mount can be maintained in position with vertebrae until all desired vertebral levels are linked together. In some embodiments, the present surgical mount avoids interference with registration such that a surgeon can operate within two vertebral levels relative to an immobilized vertebral body.

In some embodiments, the surgical instrument is configured to be securable to a fixed surface, for example, an operating room table during a surgical procedure. In some embodiments, an arm of the surgical instrument is configured to mount to an operating room table and/or a robot. In some embodiments, the surgical instrument alternatively includes retractor blades.

In some embodiments, the surgical instrument is configured for use with navigational guidance and/or robotics, including for example, Mazor™ robotics systems and their components (Medtronic PLC, Minneapolis, Minnesota, USA), having surgical components connected to a patient's spine. In some embodiments, the present surgical instrument includes aesthetic and/or ergonomic features.

In some embodiments, the surgical instrument of the present disclosure includes a surgical mount that is configured for disposal with a surgical site and is employed with a method for treating a spine. In some embodiments, the surgical mount is configured to connect a first vertebral segment or body to a second vertebral segment or body to stabilize the vertebral segments or bodies and adjacent vertebral segments or bodies for improved rigidity relative to an unconnected or singularly stabilized vertebral segment or body. In some embodiments, the surgical mount is connected to selected vertebral bodies that are disposed higher or lower relative to the surgical mount. In some embodiments, the method includes the step of connecting pins with a minimally invasive surgical technique (MIST) bridge and vertebral tissue, for example, the spinous process of thoracic vertebrae T11 and T12. In some embodiments, the method includes the step of registering one or more components of the surgical system with robotic and/or navigation guidance. See, for example, similar surgical navigation systems, robotic systems and their related components and use as described in U.S. Pat. No. 10,751,127, the entire contents of which being incorporated by reference herein. In some embodiments, registering includes implementing an O-arm for surgical planning and/or a C-arm for fluoroscopic registration. In some embodiments, vertebral levels are registered including thoracic vertebral levels T6 to T10.

In some embodiments, an incision is created with a scalpel in the skin of a patient. In some embodiments, after the incision is created, a cannula is placed with a dilator. In some embodiments, the method includes the step of fixing a first pin at thoracic vertebra T10. In some embodiments, during fixation, a pin driver is used to install the first pin, for example, a Schanz pin into a pedicle of thoracic vertebra T10 through the cannula. In some embodiments, the method includes the step of fixing the second pin at thoracic vertebra T8 in the same manner as the first pin. In some embodiments, the method includes the step of connecting a first arm and a second arm of the surgical mount with thoracic vertebrae T10 and T8. In some embodiments, the driver tightens the pin disposed with thoracic T8 to stabilize the pin such that no movement of the spine is observed. In some embodiments, the method includes the step of fixing a third pin to thoracic vertebra T6. In some embodiments, the third pin is fixed in the same manner as the first pin and the second pin. In some embodiments, the method includes the step of connecting the first arm and the second arm of the surgical mount to thoracic vertebrae T8 and T6. In some embodiments, the arms are connected in the same manner as above such that no movement of the spine is observed.

In some embodiments, the method includes the step of fixing a bone fastener, for example, a bone screw at a right side of thoracic vertebra T7. In some embodiments, the method includes the step of fixing a bone screw at a right side of thoracic vertebra T9. In some embodiments, the method includes the step of fixing a bone screw at a left side of thoracic vertebra T6. In some embodiments, the method includes the step of fixing a bone screw at a left side of thoracic vertebra T7. In some embodiments, the method includes the step of removing the surgical mount including the first arm and second arm from the surgical site, such that no movement of the spine is observed. In some embodiments, the method includes the step of removing the third pin such that no movement of the spine is observed. In some embodiments, a selective amount of force is applied to the third pin to remove the third pin. In some embodiments, the method includes the step of fixing a bone screw at right side of thoracic vertebra T6. In some embodiments, a drill is employed to drill 30 mm into thoracic vertebra T6. In some embodiments, the method includes the step of re-registration of components of the surgical system. In some embodiments, a C-arm is employed to re-register the components. In some embodiments, the method includes the step of comparing planned trajectories of the bone screws to actual bone screw placement. In some embodiments, the step of comparing includes a visual comparison.

In some embodiments, prior to a surgical procedure, a patient can be positioned in a prone or lateral position on an operating table. In some embodiments, operative levels for treatment include vertebra at the thoracic level, for example, T6 to T10. In some embodiments, bone fasteners can be delivered to the surgical site though robotic guidance and include screw shanks having 6.5 mm×40 mm dimensions.

In some embodiments, the surgical instrument of the present disclosure includes a surgical mount that is configured for insertion into a surgical site and is employed with a method for treating a spine. In some embodiments, the surgical mount is connected to selected vertebrae. In some embodiments, the method includes the step of fixing a bone mount element, for example, a first pin into the lowest pedicle of a selected vertebra. In some embodiments, the pin is fixed manually. In some embodiments, the first pin is fixed via robotic guidance, similar to that described herein. In some embodiments, the method includes the step of attaching a short bone mount (SBM) bridge to the pin. In some embodiments, the method includes the step of registering vertebral levels with robotic and/or navigation guidance. In some embodiments, the method includes the step of fixing a second pin. In some embodiments, the second pin is fixed via robotic guidance. In some embodiments, the method includes the step of positioning the surgical mount with the first and second pins. In some embodiments, the surgical mount engages the pins with a minimal amount of force. In some embodiments, the method includes the step of fixing screws and/or shanks between and above the second pin. In some embodiments, the method includes the step of fixing a third pin. In some embodiments, the third pin is fixed via robotic guidance. In some embodiments, the method includes the step of positioning a second surgical mount at the surgical site. In some embodiments, the method includes the step of fixing the bone screws and/or shanks between and above the third pin. In some embodiments, the method includes the step of fixing a fourth pin. In some embodiments, the fourth pin is fixed via robotic guidance. In some embodiments, the method includes the step of fixing a third surgical mount at the surgical site. In some embodiments, the method includes the step of fixing bone screws and/or shanks between and below the fourth pin. In some embodiments, the method includes the step of removing the pins and surgical mounts from the surgical site. In some embodiments, the method includes the step of moving the robot away from the surgical site. In some embodiments, the method includes the step of fixing bone screws and/or shanks into pin holes formed by the pins.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone, and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of surgical systems and related methods of employing a surgical system in accordance with the principles of the present disclosure. Alternate embodiments are also disclosed. Reference is made in detail to the exemplary embodiments of the present disclosure, which are illustrated in the accompanying figures. Turning to FIGS. 1-19, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate such as hydroxyapatite (HA), corraline HA, biphasic calcium phosphate, tricalcium phosphate, or fluorapatite, tricalcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected, or include fastening elements and/or instruments, as described herein.

Surgical system 10 includes a surgical instrument, for example, a surgical mount 12. In some embodiments, surgical mount 12 is configured to connect a first vertebra to a second vertebra to stabilize the vertebrae and/or adjacent vertebrae for improved rigidity relative to an unconnected or singularly stabilized vertebra. In some embodiments, surgical mount 12 improves modularity and ease of interconnection and attachment of instrument components with a surgical apparatus, surgical navigation, robotics and/or vertebrae. Surgical mount 12 includes members including an arm 14 and an arm 16. Arm 14 and/or arm 16 are configured for poly axial movement relative to a frame 42 and are configured to provide selective orientation, positioning and/or fixation of a bone element, a surgical instrument and/or support of patient anatomy, for example, for engagement and/or fixation with surrounding tissue, for example, vertebral surfaces including vertebrae.

Figure 2:
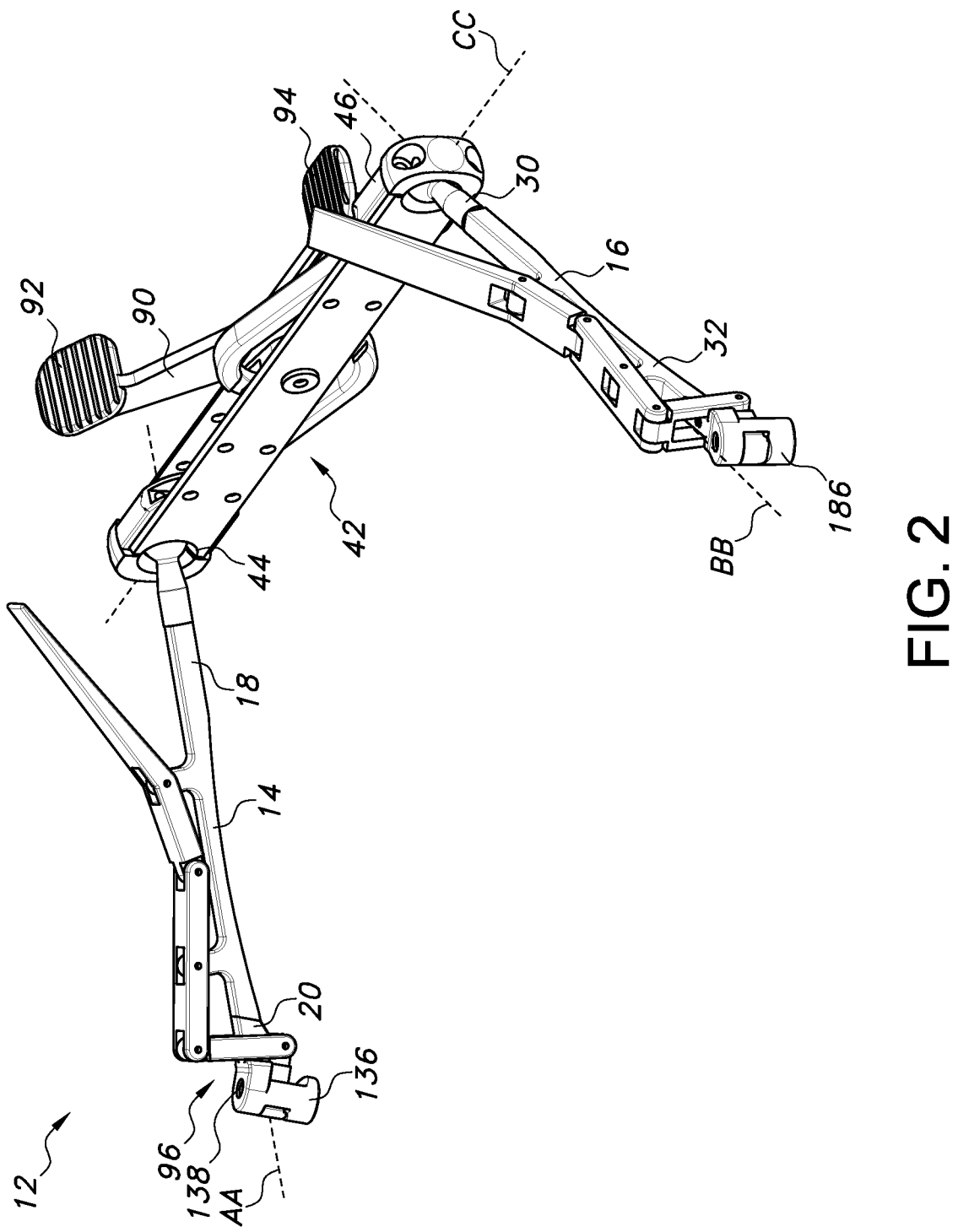
FIG. 2 is a perspective view of the components shown in FIG. 1.

Arm 14 includes an end 18 and an end 20, and defines a longitudinal axis AA, as shown in FIG. 2. Arm 14 may have various cross-section configurations, for example, arcuate, cylindrical, oblong, rectangular, polygonal, undulating, irregular, uniform, non-uniform, consistent, variable, and/or U-shape. In some embodiments, arm 14 includes a cross-section configured to aid in visualization during x-ray and/or fluoroscopy. In some embodiments, arm 14 may have alternate surface configurations, for example, rough, undulating, corrugated, porous, semi-porous, dimpled, polished and/or textured.

Figure 4:
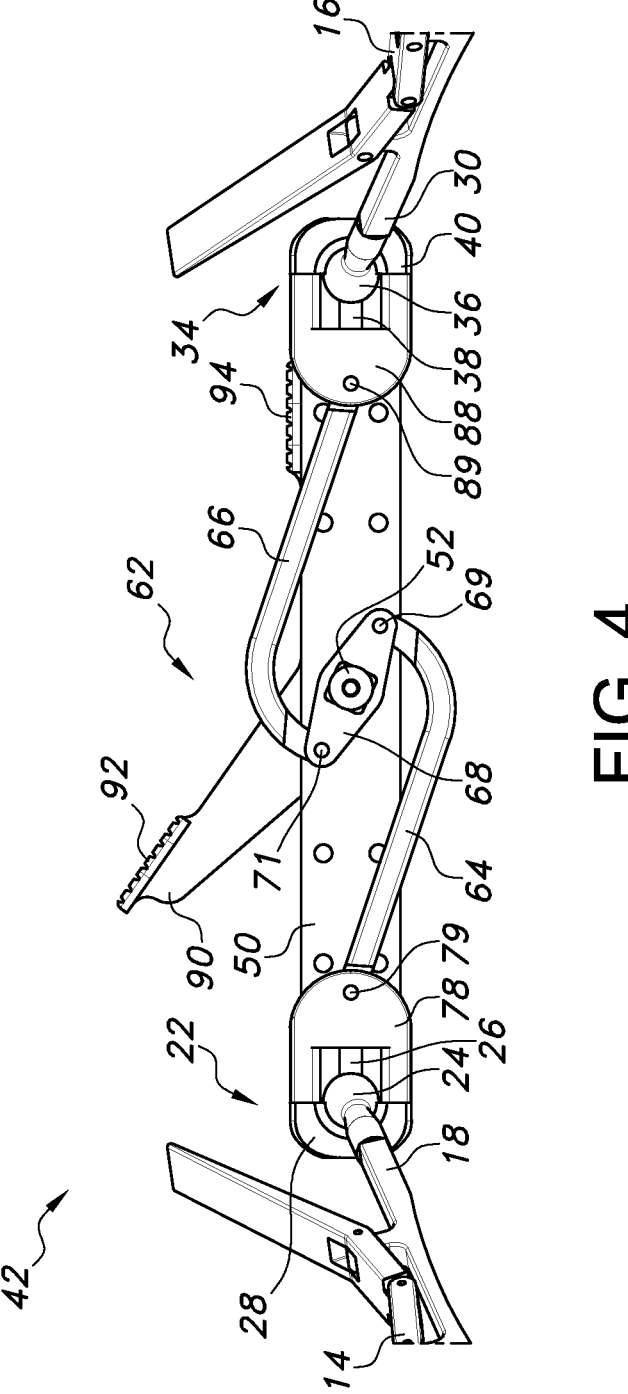
FIG. 4 is a cutaway view of components shown in FIG. 1.
Figure 5:
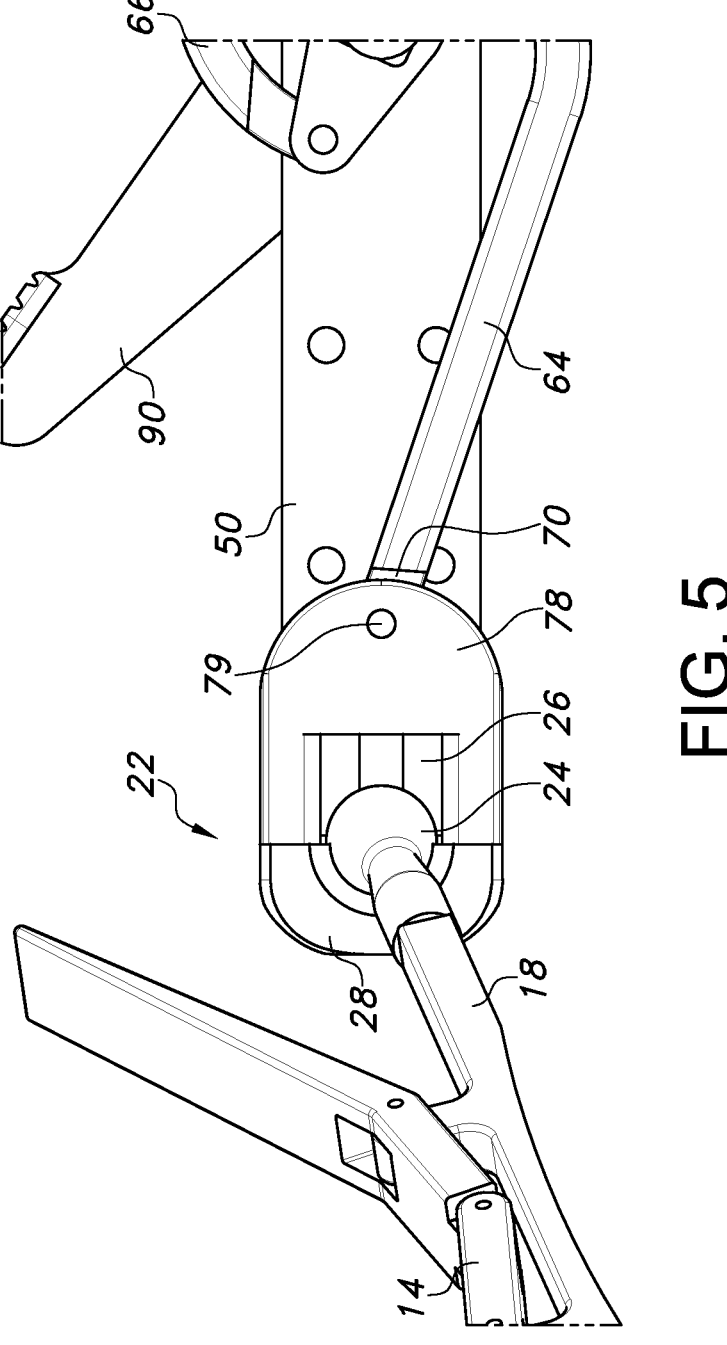
FIG. 5 is a cutaway view of components shown in FIG. 4.

End 18 includes at least a portion of a spheroidal joint 22, including a spherical part 24, as shown in FIG. 4. Spherical part 24 is configured for engagement with portions of spheroidal joint 22, for example, a socket 26 formed from a portion of an end cap 28 and a portion of a plate 78 of a link 64, described herein. Socket 26 is movable relative to spherical part 24 between a non-locking orientation and a locking orientation via a linkage 62 described herein. In the non-locking orientation, socket 26 is movable relative to spherical part 24 and in the locking orientation, socket 26 is fixable with spherical part 24 to lock arm 16 relative to arm 14, frame 42, vertebral surfaces and/or implants, as described herein. In some embodiments, spheroidal joint 22 alternatively includes a condyloid joint or ellipsoid joint, a saddle joint, a hinge joint and/or a pivot joint. In some embodiments, spherical part 24 includes a ball. In some embodiments, spherical part 24 can include an elliptical, conical, semispherical, and/or oval shape.

Arm 16 includes an end 30 and an end 32, and defines a longitudinal axis BB, as shown in FIG. 2. Arm 16 may have various cross-section configurations, for example, arcuate, cylindrical, oblong, rectangular, polygonal, undulating, irregular, uniform, non-uniform, consistent, variable, and/or U-shape. In some embodiments, arm 16 includes a cross-section configured to aid in visualization during x-ray and/or fluoroscopy. In some embodiments, arm 16 may have alternate surface configurations, for example, rough, undulating, corrugated, porous, semi-porous, dimpled, polished and/or textured. In some embodiments, surgical mount 12 may include one or a plurality of arms.

End 30 includes at least a portion of a spheroidal joint 34, including a spherical part 36, as shown in FIG. 4. Spherical part 36 is configured for engagement with portions of spheroidal joint 34, for example, a socket 38 formed from a portion of an end cap 40 and a portion of a plate 88 of a link 66, described herein. Socket 38 is movable relative to spherical part 36 between the non-locking orientation and locking orientation via linkage 62 described herein. In the non-locking orientation, socket 38 is movable relative to spherical part 36 and in the locking orientation, socket 38 is fixable with spherical part 36 to lock arm 16 relative to arm 14, frame 42, vertebral surfaces and/or implants, as described herein. In some embodiments, spheroidal joint 34 alternatively includes a condyloid joint or ellipsoid joint, a saddle joint, a hinge joint and/or a pivot joint. In some embodiments, spherical part 36 includes a ball. In some embodiments, spherical part 36 can include an elliptical, conical, semispherical, and/or oval shape.

Figure 3:
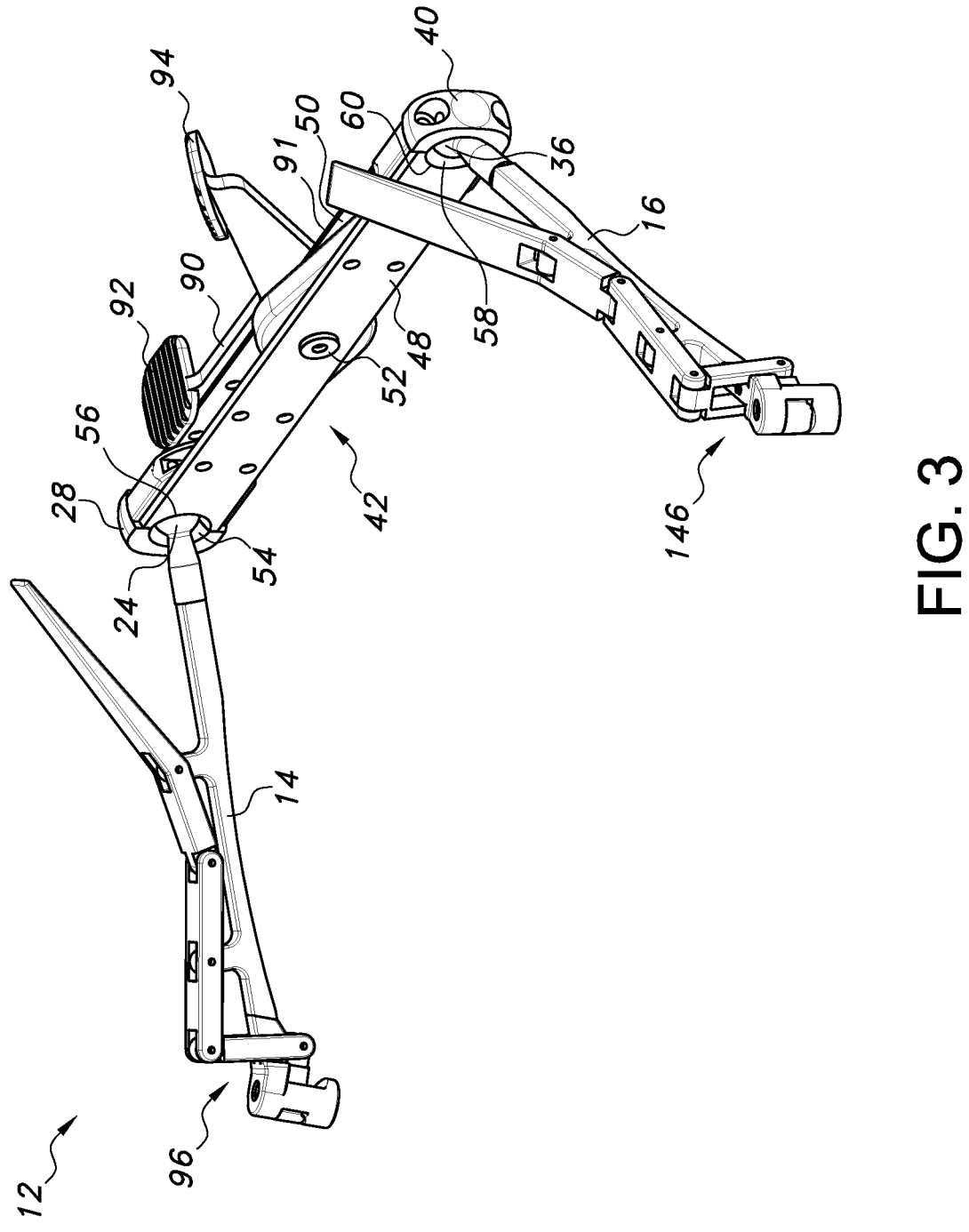
FIG. 3 is a perspective view of the components shown in FIG. 1.

Sockets 26, 38 are supported with frame 42 such that sockets 26, 38 are movable relative to frame 42 between the non-locking orientation and the locking orientation. Frame 42 includes an end 44 and an end 46, and defines a longitudinal axis CC, as shown in FIG. 2. Frame 42 includes a side 48 and a side 50, as shown in FIGS. 3 and 4. Side 48 is fixed with side 50 via a rotatable fastener 52. An end portion 56 of side 48 and a surface of end cap 28 form an opening 54 configured for disposal of spherical part 24 of arm 14, and an end portion 60 of side 48 and a surface of end cap 40 form an opening 58 configured for disposal of spherical part 36 of arm 16. In some embodiments, end portions 56, 60 and/or surfaces of end caps 28, 40 can include various surface configurations including arcuate, tapered, concave and/or planar.

Figure 10:
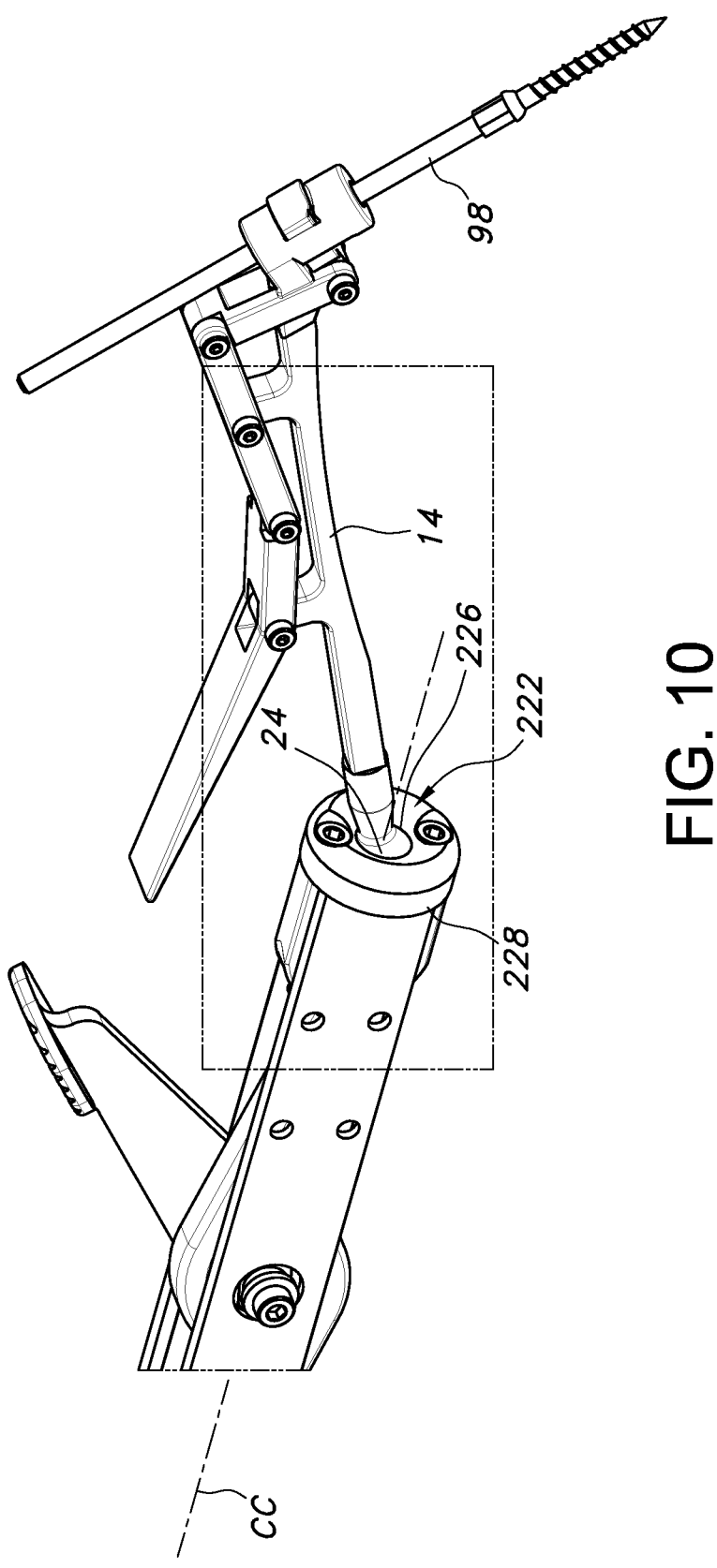
FIG. 10 is a perspective view of components of one embodiment of a surgical system in accordance with the principles of the present disclosure.
Figure 11:
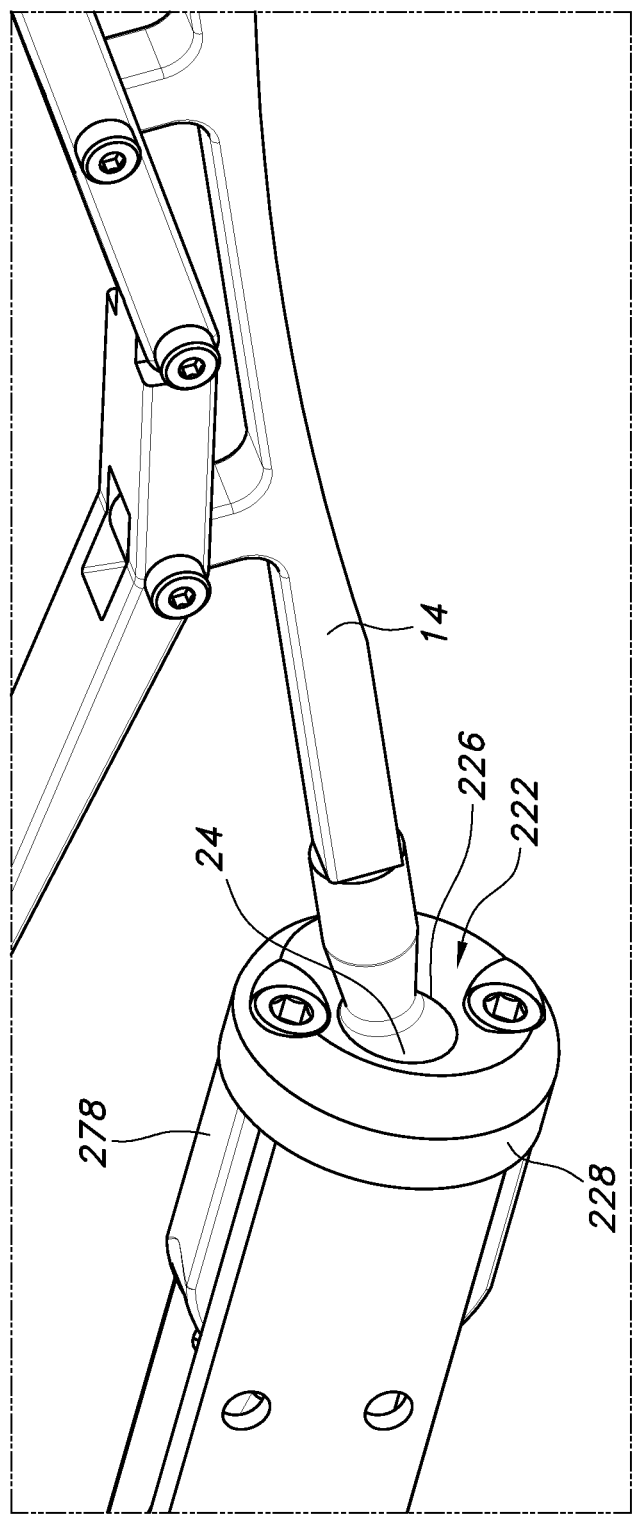
FIG. 11 is an enlarged perspective view of components shown in FIG. 10.

In one embodiment, as shown in FIGS. 10 and 11, surgical mount 12 can include one or more spheroidal joints 222, similar to spheroidal joints 22, 34, as described herein. Spheroidal joint 222 includes a socket 226 including a portion of an end cap 228 and a portion of plate 278, similar to plates 78, 88 as described herein. Components of socket 226 are movable, similar to that described herein, for engagement with spherical parts 24, 36. End cap 228 is in alignment with frame 42 along longitudinal axis CC, which is configured as an inline center linkage mechanism.

Figure 9:
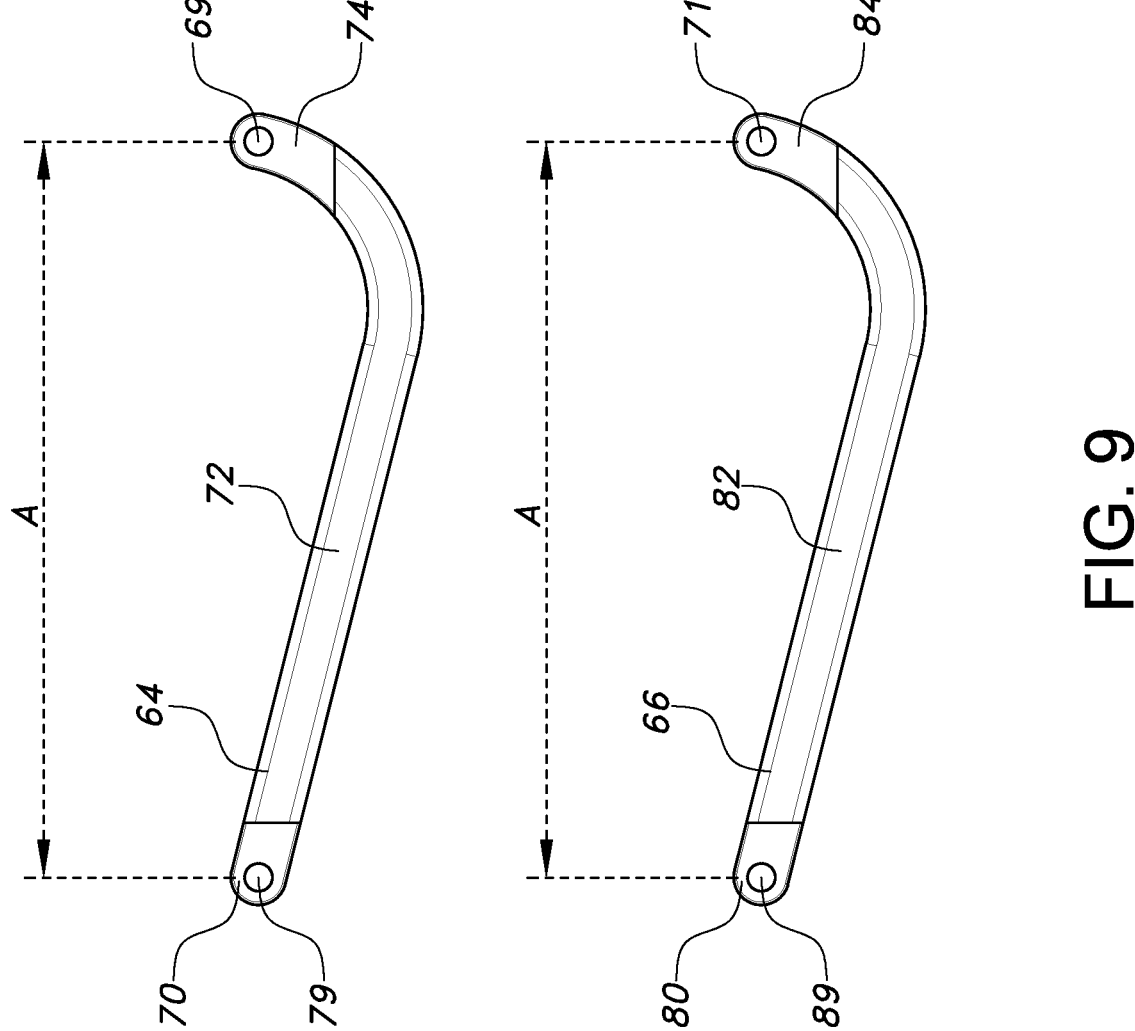
FIG. 9 is a plan view of components shown in FIG. 1.

Surgical mount 12 includes a linkage 62 that attaches to sides 48, 50 of frame 42 via fastener 52. Linkage 62 is configured to move sockets 26, 38 between the non-locking orientation and locking orientation to fix arm 14 and/or arm 16 relative to frame 42, components of system 10 and/or vertebrae. Linkage 62 includes a link 64 and a link 66, as shown in FIGS. 4 and 9. Link 64 is connected to link 66 via a connector plate 68. Links 64, 66 include curvature for connection to frame 42 and facilitate locking. In some embodiments, link 64 and/or link 66 may have alternate configurations, for example, linear, undulating, irregular, uniform, non-uniform, consistent, and/or angled.

Figure 6:
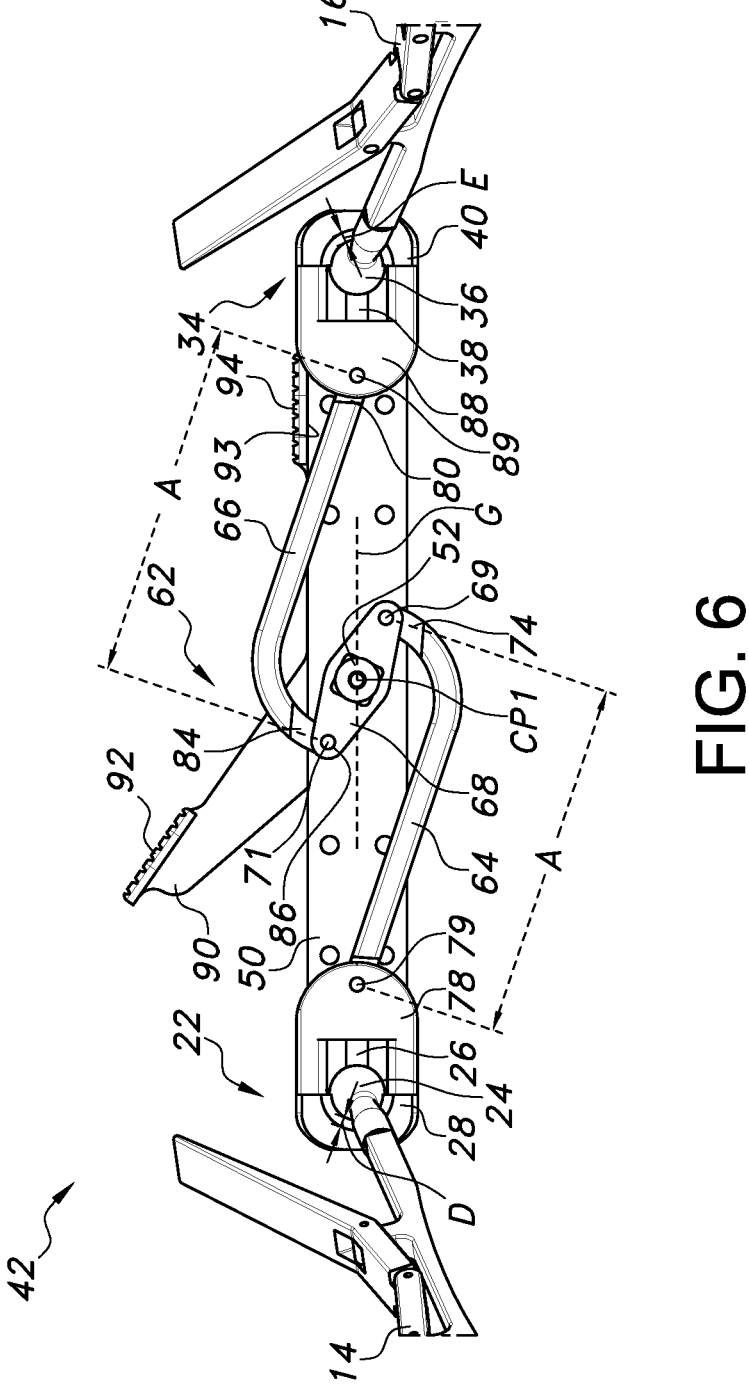
FIG. 6 is a cutaway view of components shown in FIG. 1.

Link 64 includes an end 70, an intermediate portion 72 and an end 74, as shown in FIG. 9. End 74 engages an end 76 of plate 68, as shown in FIG. 6. Link 64 includes plate 78 that is attached to link 64 via a pin 79. Plate 78 is moved via link 64 to draw a surface of end cap 28 into fixation with spherical part 24 to dispose socket 26 in the locking orientation. Link 66, similar to link 64 includes an end 80, an intermediate portion 82 and an end 84. End 84 engages an end 86 of plate 68, as shown in FIG. 6. Link 66 includes plate 88 that is attached to link 66 via a pin 89. Plate 88 is moved via link 66 to draw a surface of end cap 40 into fixation with spherical part 36 to dispose socket 38 in the locking orientation. In some embodiments, plates 78, 88 may have various cross-section configurations, for example, arcuate, cylindrical, oblong, rectangular, polygonal, undulating, irregular, uniform, non-uniform, consistent, and/or variable.

Figure 8:
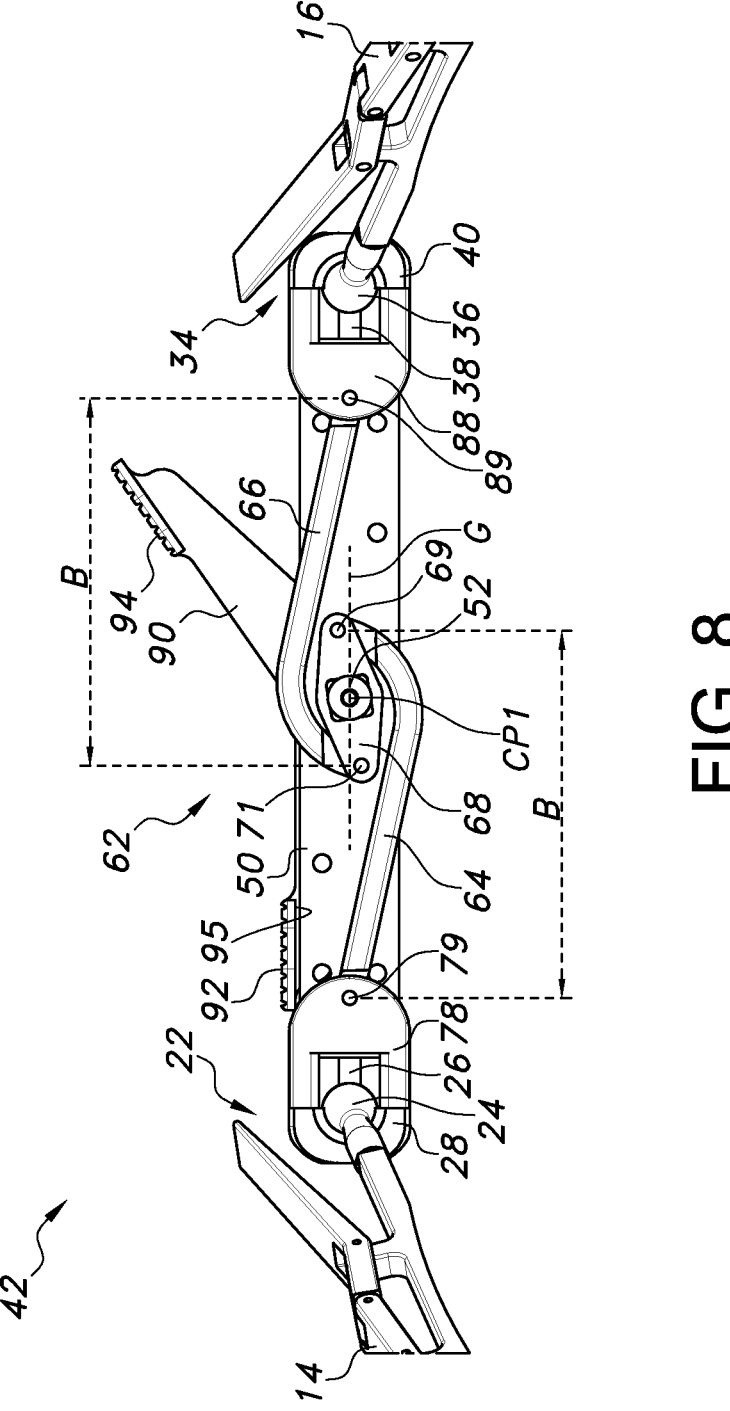
FIG. 8 is a cutaway view of components shown in FIG. 1.

Linkage 62 includes a lever 90 including handles 92, 94. Lever 90 engages an outer surface 91 of side 50 and connects to linkage 62 via fastener 52. Lever 90 is connected with links 64, 66 and is rotatable relative to frame 42 between a limit surface 93 in the non-locking orientation, as shown in FIG. 6, and a limit surface 95 in the locking orientation, as shown in FIG. 8.

In the non-locking orientation, spherical parts 24, 36 are movable within sockets 26, 38 and handle 94 is movable to limit surface 93 to prevent a center pivot CP1 from rotating in a clockwise direction and lever 90 from rotating beyond limit surface 93, as shown in FIG. 6. In the non-locking orientation, pin 79 and a pin connection 69 of link 64 and plate 68 measure a length A such that a clearance exists between end cap 28 and spherical part 24, as shown by arrow D in FIG. 6. The clearance facilitates poly axial movement of arm 14 relative to frame 42. Pin 89 and a pin connection 71 of link 66 and plate 68 measure length A such that a clearance exists between end cap 40 and spherical part 36, as shown by arrow E. The clearance facilitates poly axial movement of arm 16 relative to frame 42.

Figure 7:
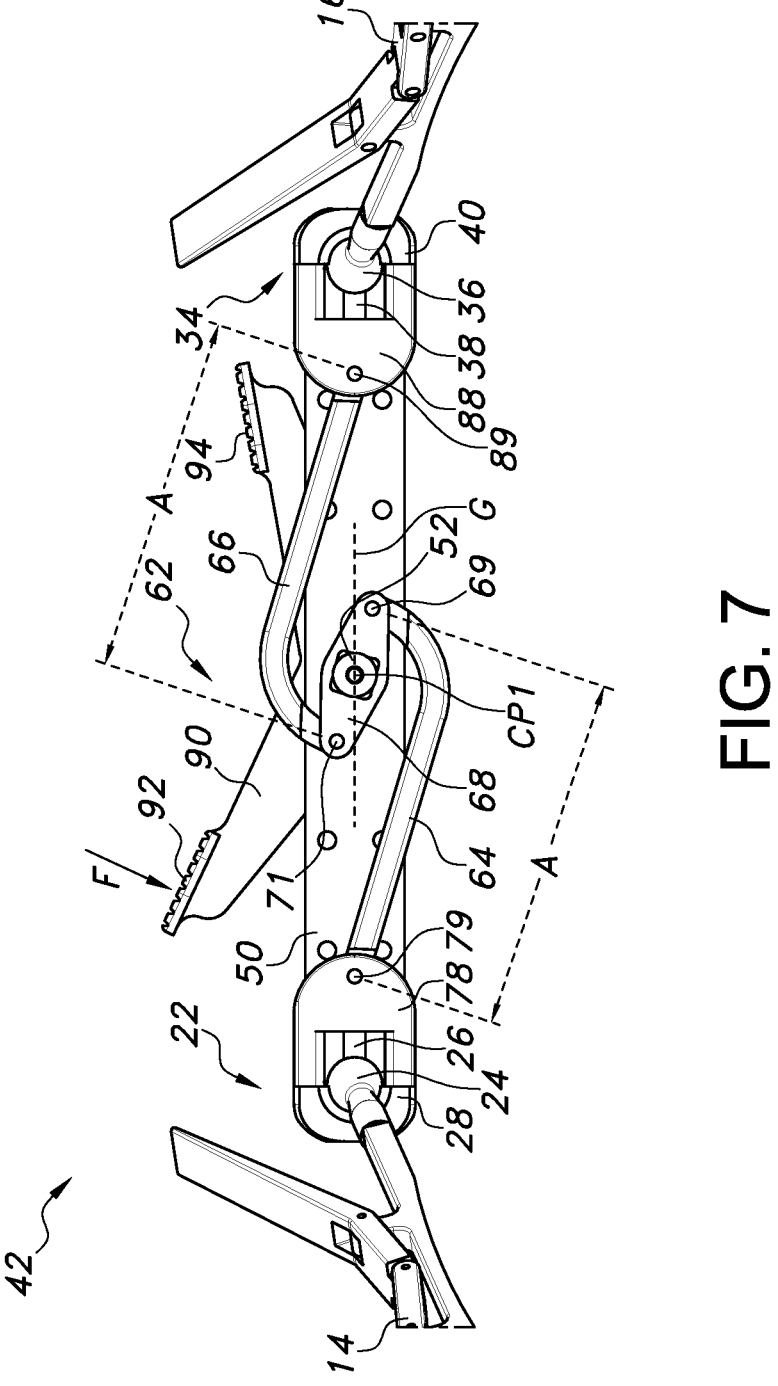
FIG. 7 is a cutaway view of components shown in FIG. 1.

To move spheroidal joints 22, 34 into the locking orientation, a force is applied to depress handle 92 in a downward direction, as shown by arrow F in FIG. 7, for movement of lever 90 to limit surface 95 to prevent center pivot CP1 from rotating in a counterclockwise direction and lever 90 from rotating beyond limit surface 93. Links 64, 66 rotate with plate 68 and elastically deform beyond an over-center position to move linkage 62 beyond a central axis G, as shown in FIGS. 7 and 8. Links 64, 66 simultaneously draw end caps 28, 40 inwardly to eliminate the clearance between end caps 28, 40 and spherical parts 24, 36 such that end caps 28, 40 frictionally engage spherical parts 24, 36. Links 64, 66 rotate and deform under tension such that pin 79 and pin connection 69 measure a length B, and pin 89 and pin connection 71 measure the length B, as shown in FIG. 8. Length B is greater than length A such that links 64, 66 are disposed in the over center position to releasably fix linkage 62 and spheroidal joints 22, 34 in the locking orientation.

End 20 of arm 14 includes a lock 96, as shown in FIGS. 12-17. Lock 96 is configured for engagement with a bone element, for example, a bone pin 98. Lock 96 includes links 100, 102 and 104 connected in series with arm 14. Links 100, 102, 104 are connected to form an over-center linkage and connection with a plate 106 to move plate 106 between a non-locking orientation and a locking orientation with pin 98. An inner surface 108 of plate 106 frictionally engages pin 98 to fix arm 14 with pin 98.

Figure 14:
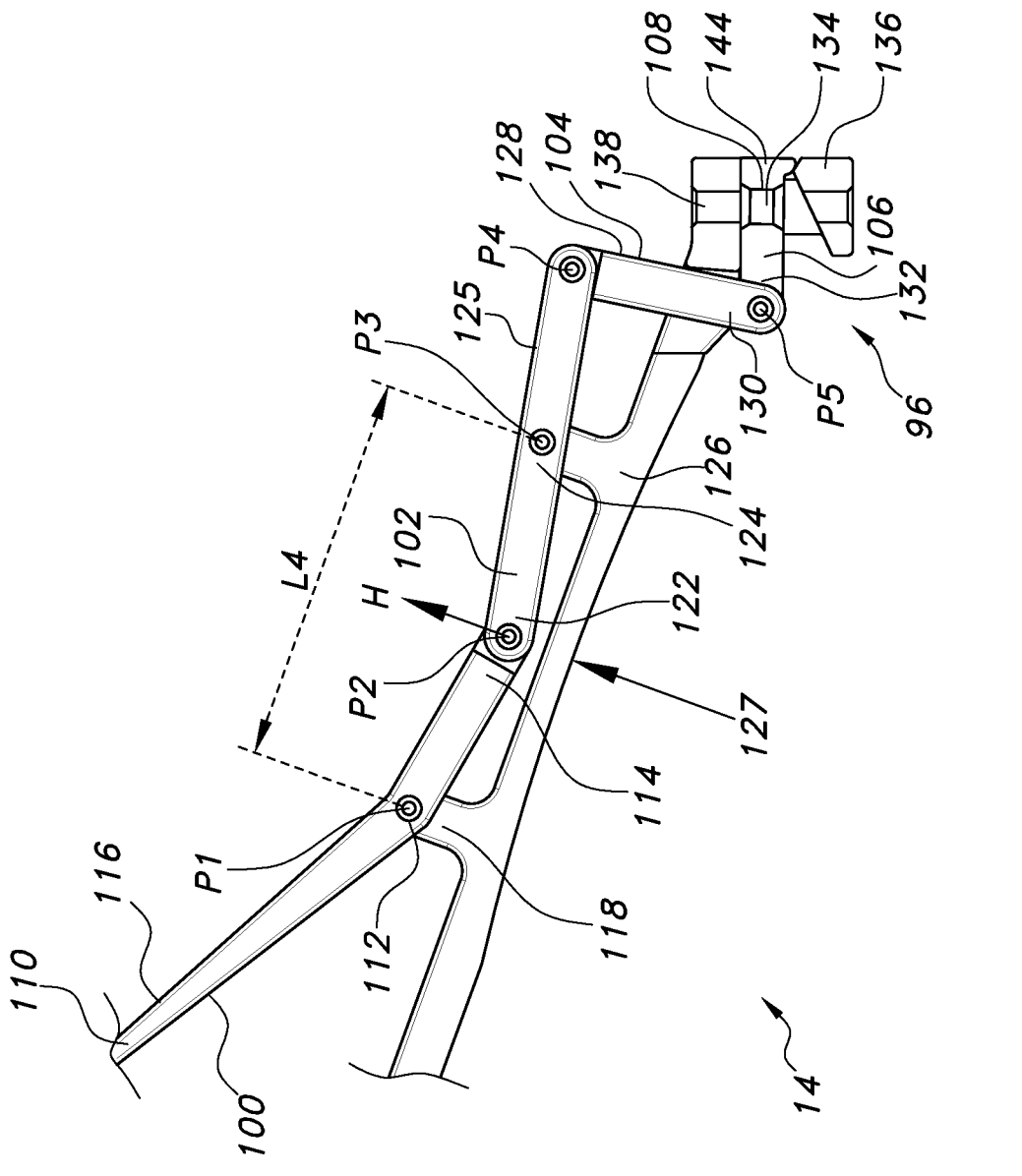
FIG. 14 is a side view of components shown in FIG. 1.

Link 100 includes an end 110, an intermediate portion 112 and an end 114, as shown in FIG. 14. End 110 includes a lever 116. Portion 112 is connected to a portion 118 of arm 14 for rotation at a pivot point P1. End 114 is connected to an end 122 of link 102 for relative rotation at a pivot point P2. Link 102 includes end 122, an intermediate portion 124 and an end 125. Portion 124 is connected to a portion 126 of arm 14 for rotation at a pivot point P3. End 125 is connected to an end 128 of link 104 for relative rotation at a pivot point P4. Link 104 includes end 128 and an end 130. End 130 is connected to an end 132 of plate 106 for relative rotation at a pivot point P5. In some embodiments, pivots P1 to P5 can include a pivot pin and/or a hinge pin.

Figure 16:
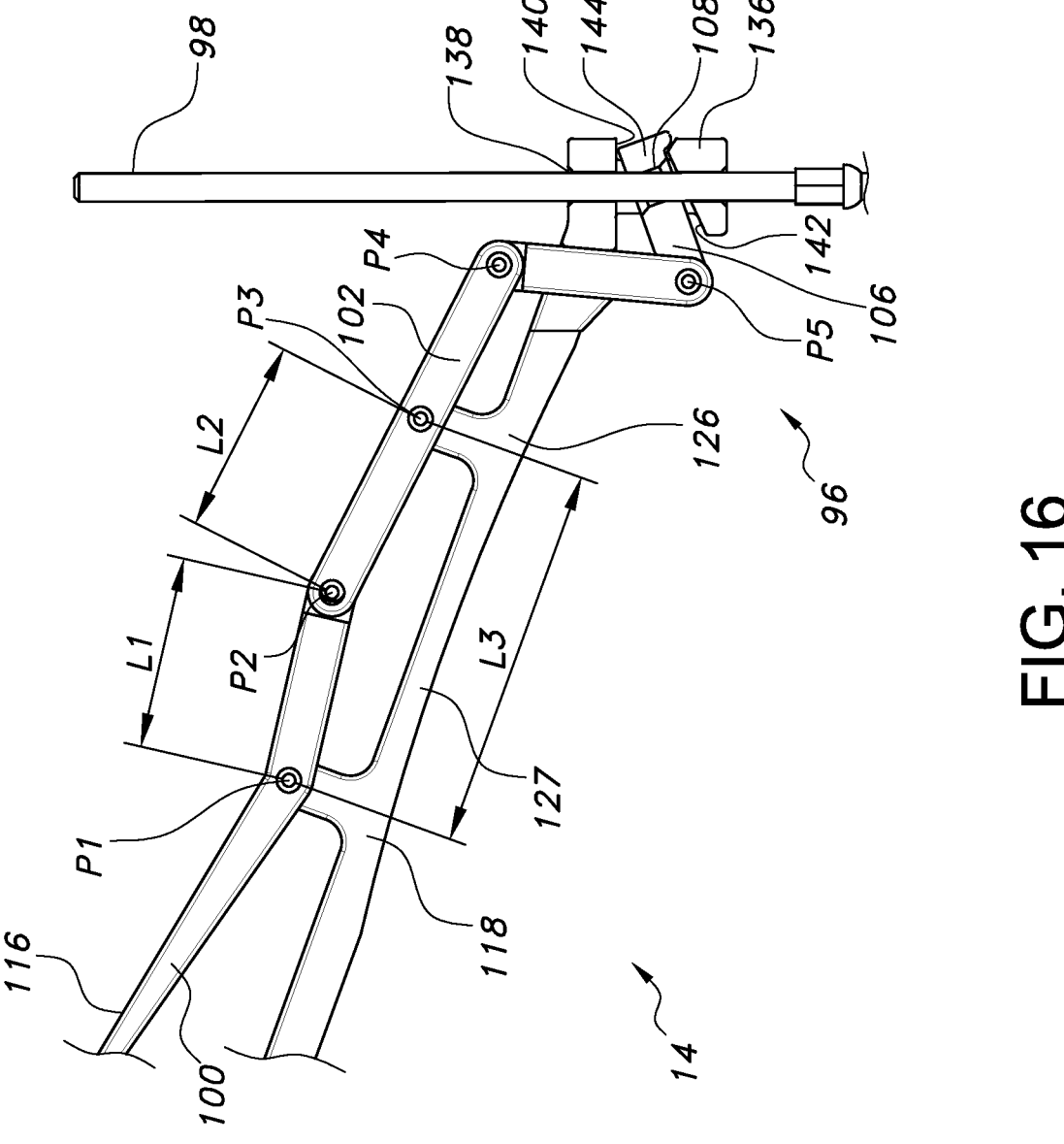
FIG. 16 is a side view of components shown in FIG. 1.

Links 100, 102, 104 are connected to form an over-center linkage, for example, a length L1 is measured between pivot P1 and pivot P2, as shown in FIG. 16. A length L2 is measured between pivot P2 and pivot P3, and a length L3 is measured between portion 118 of arm 14 and portion 126 of arm 14. A length L4 is measured between pivot P1 and pivot P3, as shown in FIG. 14. Lengths L1 and L2 are greater than length L3 and a selected amount of force is applied to orient links 100, 102 in an over-center orientation. Length L3 is less than lengths L1 and L2 to facilitate management of the force exerted upon arm 14. When a selected amount of force is applied to pivot P2 via lever 116, arm 14 will deform at a portion 127 such that pivot P2 is disposed in an over center orientation, for example, in a non-locking orientation, as shown in FIG. 14, or in a locking orientation, as shown in FIG. 16, of plate lock 106, as described herein. In an over center orientation, portion 127 is connected to pivot P2 via links 100, 102 and includes a tension force to maintain pivot P2 in the over center orientation in a non-locking orientation and/or locking orientation of links 100, 102, 104 and lock 96.

Plate 106 includes inner surface 108, as shown in FIG. 14. Surface 108 defines an opening 134 configured for disposal of pin 98. Surface 108 is configured for frictional engagement with pin 98 to fix arm 14 with pin 98. In some embodiments, surface 108 may have alternate surface configurations, for example, rough, undulating, porous, semiporous, dimpled, one or more teeth, polished and/or textured.

End 20 of arm 14 includes an engagement receptacle 136 that is configured for disposal of pin 98. Receptacle 136 includes an opening 138 configured for disposal of pin 98, a transverse opening 140 and a transverse opening 142 configured for disposal of an end 144 of plate 106 when plate 106 frictionally engages pin 98, as shown in FIG. 16.

Figure 12:
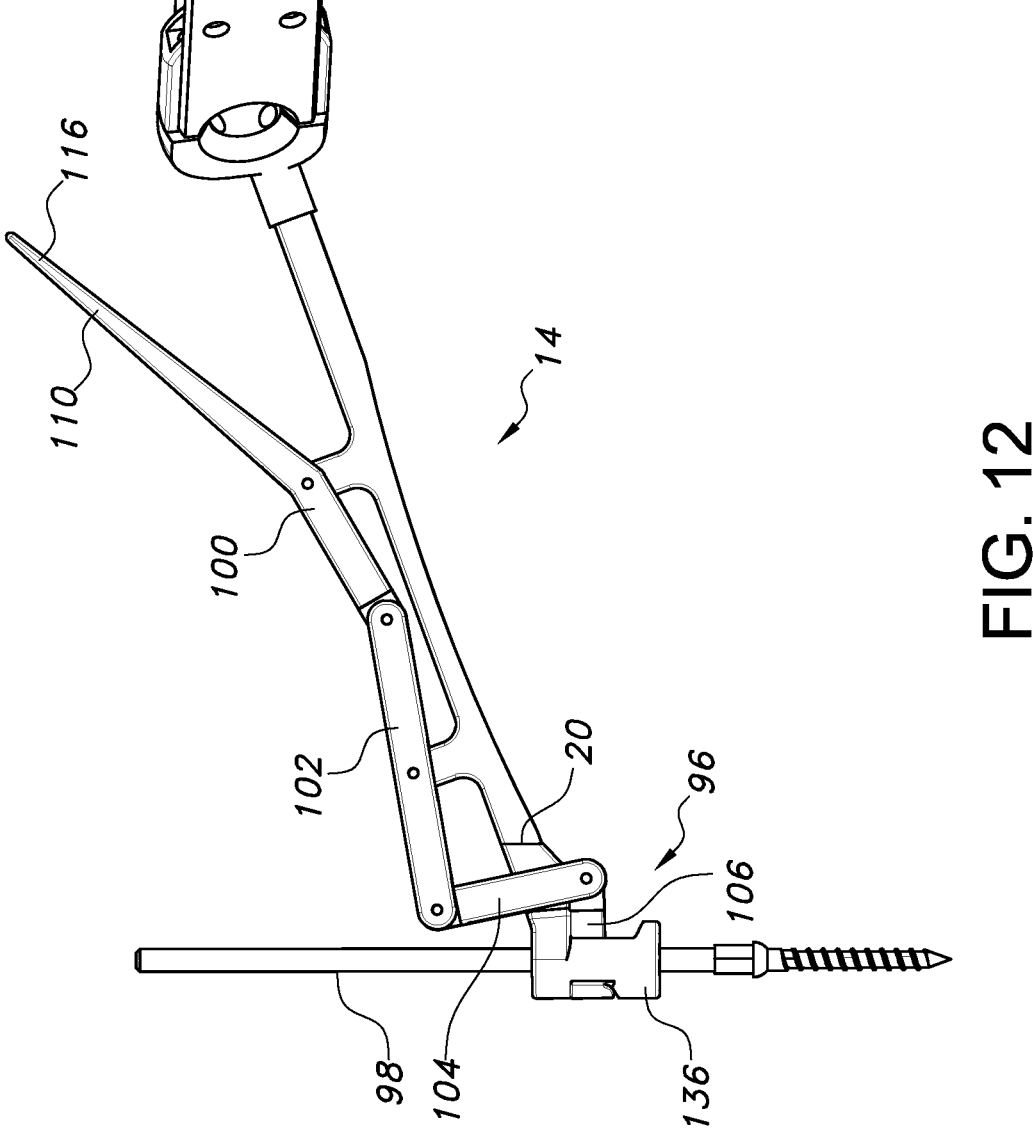
FIG. 12 is a side view of components shown in FIG. 1.
Figure 13:
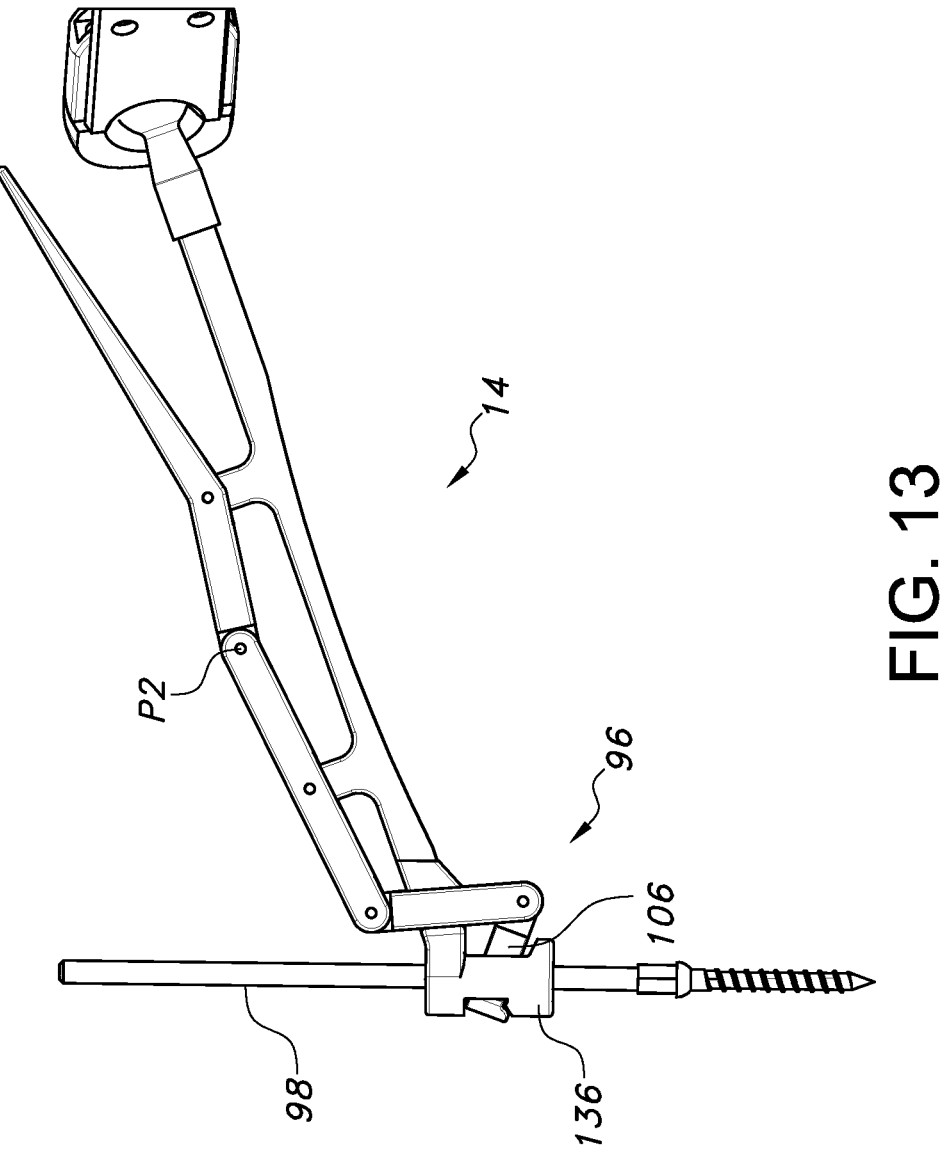
FIG. 13 is a side view of components shown in FIG. 1.
Figure 15:
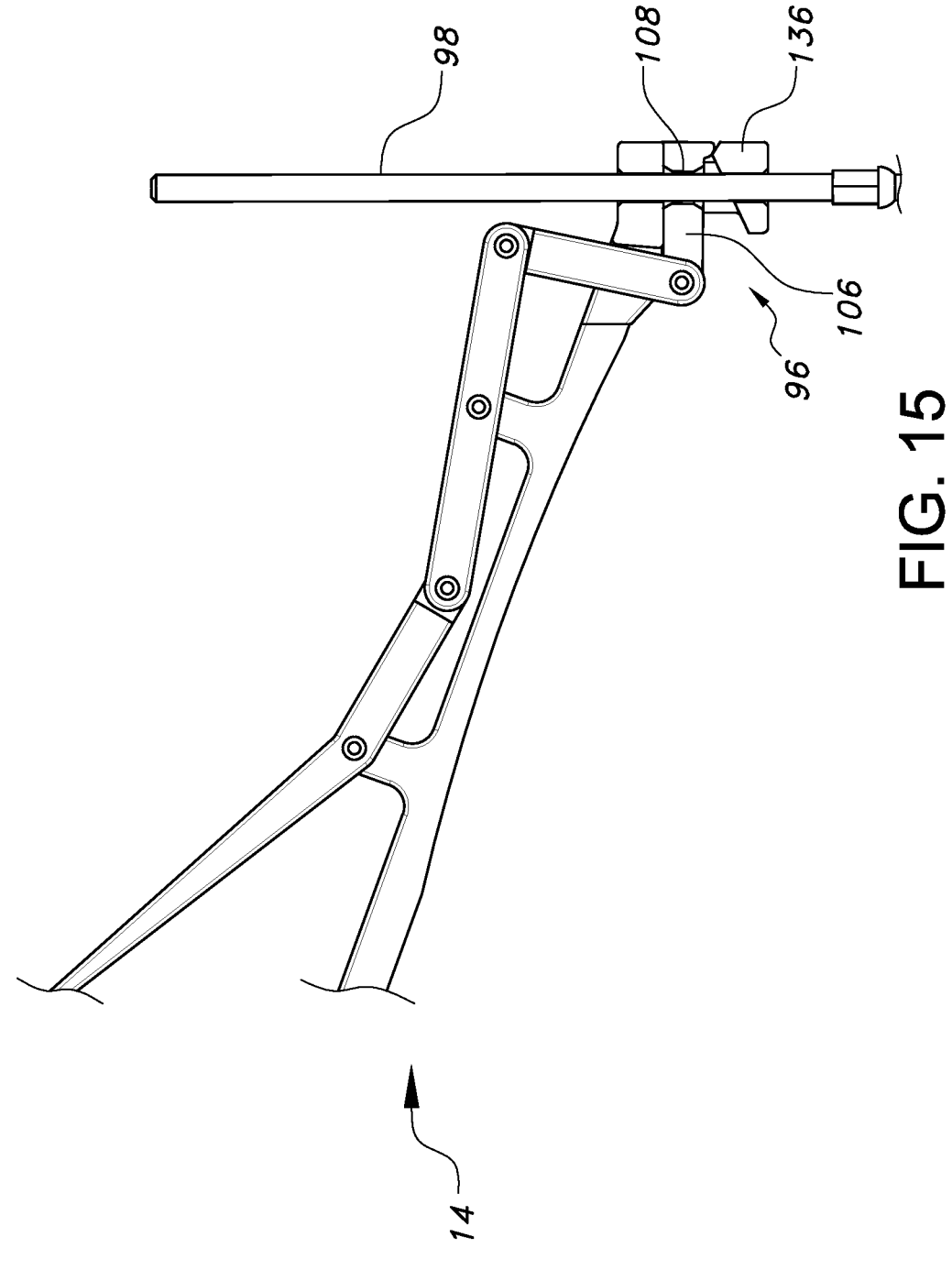
FIG. 15 is a side view of components shown in FIG. 1.
Figure 17:
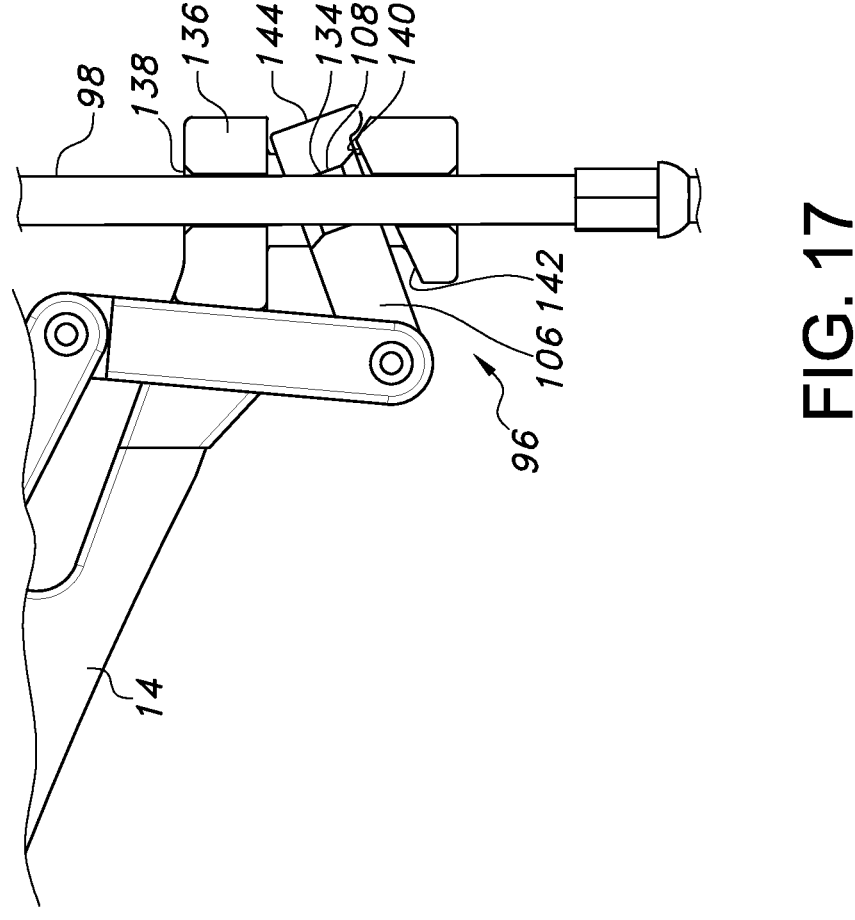
FIG. 17 is a side view of components shown in FIG. 1.

In the non-locking orientation, as shown in FIGS. 12, 14 and 15, pivot P2 is disposed in an over center orientation and plate 106 is disposed with receptacle 136 disposed in a horizontal and/or zero angle orientation relative to receptacle 136. Links 100, 102, 104 and lock 96 are maintained in the non-locking orientation via tension force of portion 127 and connection to pivot P2, as described herein. Pin 98 is free to translate relative to plate 106 and through opening 134 in the non-locking orientation. To dispose links 100, 102, 104 and lock 96 in the locking orientation such that pin 98 is fixed with arm 14, as shown in FIGS. 16 and 17, a force is applied to lever 116 such that connected links 100, 102 translate pivot P2 from the over center orientation corresponding to the non-locking orientation to the over center orientation corresponding to the locking orientation, as shown by arrow H in FIG. 14. As links 100, 102 rotate to the over center orientation corresponding to the locking orientation, link 104 connected thereto rotates plate 106 such that inner surface 108 frictional engages pin 98 disposed with opening 134 to fix pin 98 with arm 14. Links 100, 102, 104 and lock 96 are maintained in the locking orientation via tension force of portion 127 and connection to pivot P2, as described herein. In some embodiments, plate 106 is disposed at an angle relative to receptacle 136 to frictionally engage pin 98 in the locking orientation. In some embodiments, plate 106 is disposed at an angle in a range of 10 through 75 degrees relative to receptacle 136 to frictionally engage pin 98 in the locking orientation. In some embodiments, plate 106 is disposed at an angle of 45 degrees relative to receptacle 136 to frictionally engage pin 98 in the locking orientation.

Figure 18:
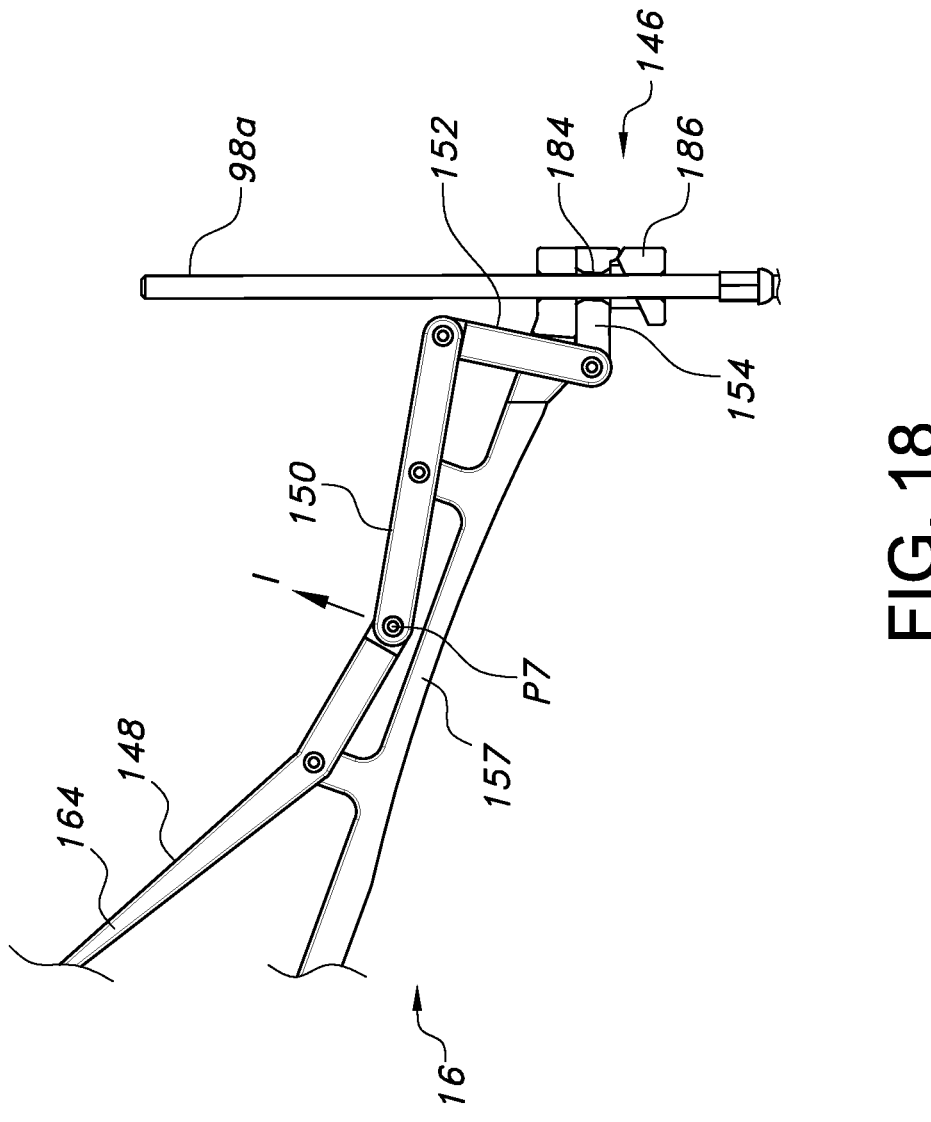
FIG. 18 is a side view of components shown in FIG. 1.
Figure 19:
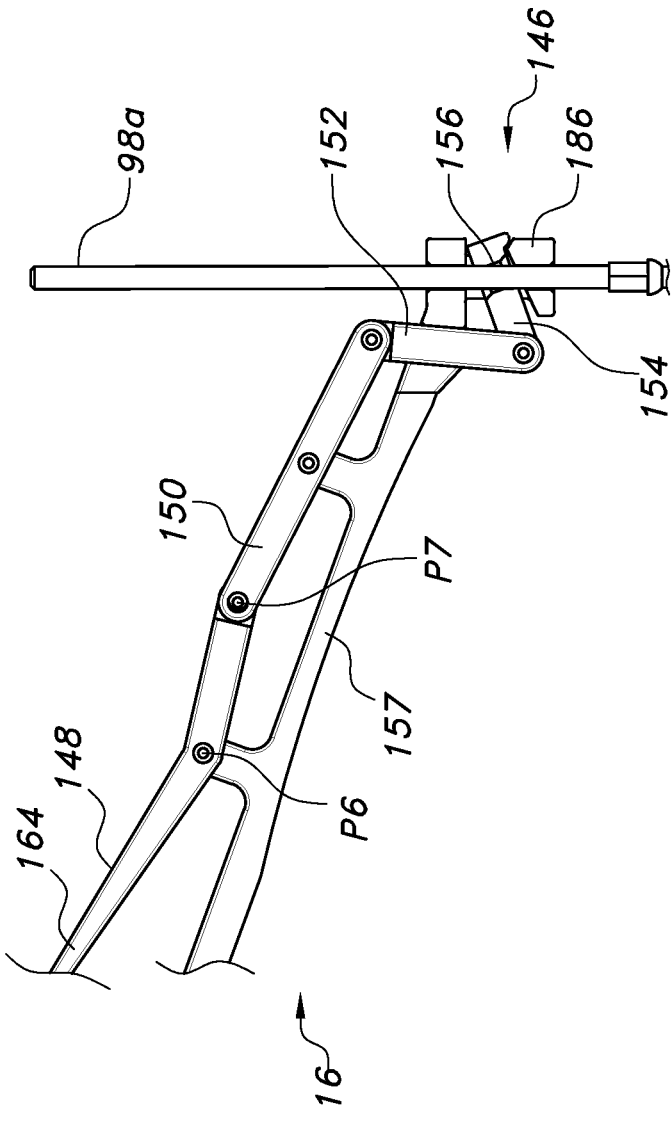
FIG. 19 is a side view of components shown in FIG. 1.

End 32 of arm 16 includes a lock 146, as shown in FIGS. 1, 18 and 19, similar to arm 14, links 100, 102, 104 and lock 96 described herein, which frictionally engages, for example, a pin 98a to fix arm 16 with pin 98a. In a non-locking orientation, as shown in FIG. 18, a pivot P7 is disposed in an over center orientation and a plate 154 is disposed with a receptacle 186 disposed in a horizontal and/or zero angle orientation relative to receptacle 186. Links 148, 150, 152 and lock 146 are maintained in the non-locking orientation via tension force of a portion 157 and connection to pivot P7, similar to portion 127 and pivot P2 described herein. Pin 98a is free to translate relative to plate 154 and a through opening 184 in the non-locking orientation. To dispose links 148, 150, 152 and lock 146 in the locking orientation such that pin 98a is fixed with arm 16, as shown in FIG. 19, a force is applied to a lever 164 such that connected links 148, 150 translate pivot P7 from the over center orientation corresponding to the non-locking orientation to the over center orientation corresponding to the locking orientation, as shown by arrow I in FIG. 18. As links 148, 150 rotate to the over center orientation corresponding to the locking orientation, link 152 connected thereto rotates plate 154 such that a surface 156 of plate 154 frictional engages pin 98a disposed with opening 184 to fix pin 98a with arm 16. Links 148, 150, 152 and lock 146 are maintained in the locking orientation via tension force of portion 157 and connection to pivot P7, similar to portion 127 and pivot P2 described herein. In some embodiments, plate 154 is disposed at an angle relative to receptacle 186 to frictionally engage pin 98a in the locking orientation. In some embodiments, plate 154 is disposed at an angle in a range of 10 through 75 degrees relative to receptacle 186 to frictionally engage pin 98a in the locking orientation. In some embodiments, plate 154 is disposed at an angle of 45 degrees relative to receptacle 186 to frictionally engage pin 98a in the locking orientation.

In some embodiments, surgical mount 12 may be employed with various surgical instruments, for example, drivers, extenders, reducers, spreaders, distractors, clamps, forceps, elevators, and drills, which may be alternately sized and dimensioned, and arranged as a kit. In some embodiments, surgical system 10 may comprise the use of microsurgical and image guided technologies, for example, surgical navigation components employing emitters and sensors, which may be employed to track introduction and/or delivery of the components of surgical system 10 including the surgical instruments to a surgical site. See, for example, the surgical navigation components and their use as described in U.S. Pat. Nos. 6,021,343, 6,725,080, 6,796, 988, the entire contents of each of these references being incorporated by reference herein.

In assembly, operation and use, surgical system 10, similar to the systems and methods described herein, is employed with a surgical procedure for treatment of a spinal disorder, such as those described herein, affecting a section of a spine of a patient. Surgical system 10 may also be employed with other surgical procedures. In some embodiments, surgical system 10 is employed to implant components, such as bone fasteners, rods, interbody devices, and plates, with a patient.

In use, to treat a selected section of vertebrae, as shown in FIGS. 20-32, a medical practitioner obtains access to a surgical site including vertebrae V, for example through incision and retraction of tissues. In some embodiments, surgical system 10 includes a percutaneous surgical implantation. In some embodiments, surgical system 10 can be used in any existing surgical method or technique including open surgery, mini-open surgery or minimally invasive surgery, whereby vertebrae V is accessed through a mini-incision, or a sleeve that provides a protected passageway to the area. Once access to the surgical site is obtained, the surgical procedure can be performed for treating the spine disorder.

Figures 20, 21, 22:
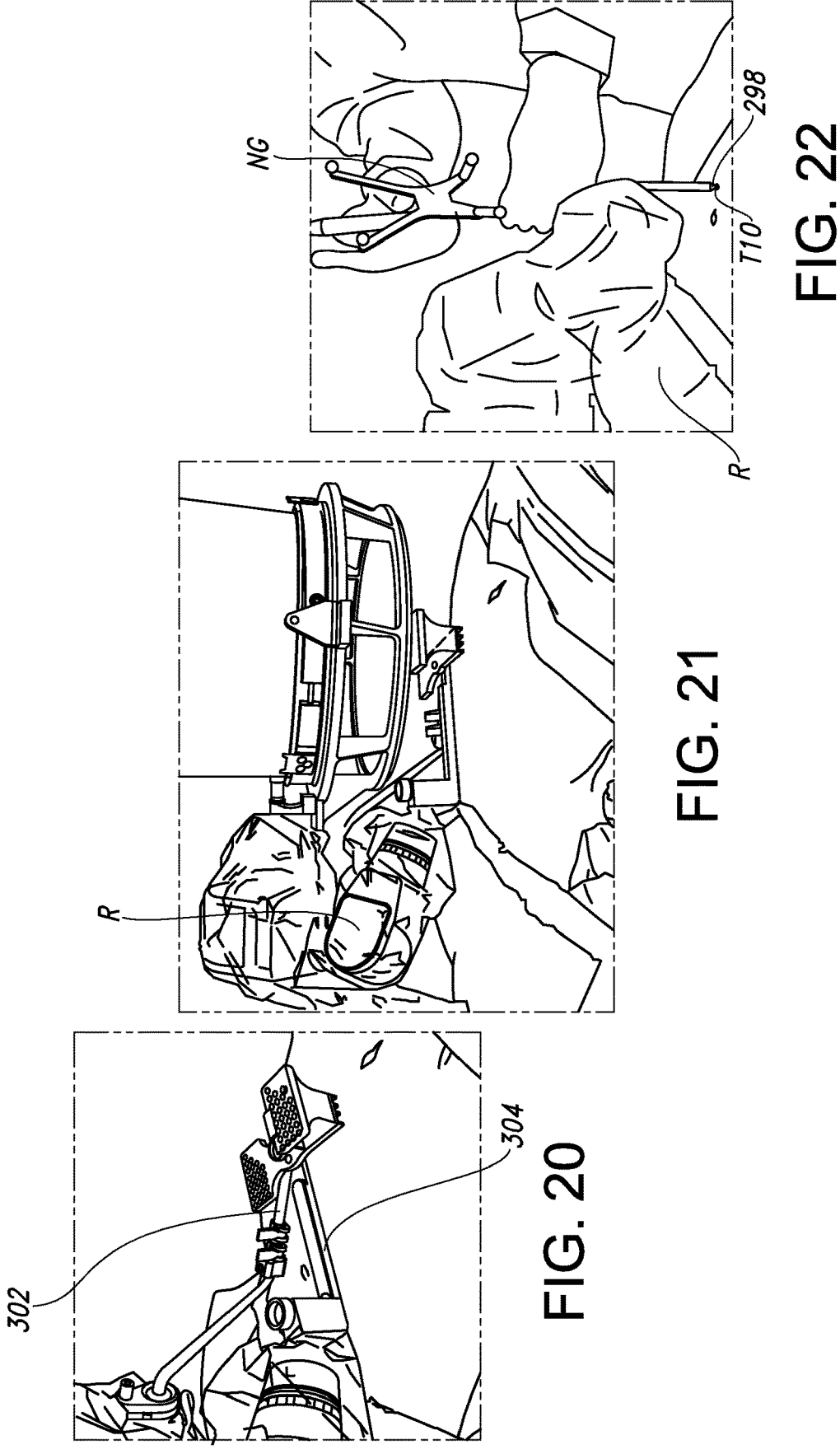
FIG. 20 is a perspective view of components of one embodiment of a surgical system in accordance with the principles of the present disclosure.
FIG. 21 is a perspective view of components of the system shown in FIG. 20.
FIG. 22 is a perspective view of components of the system shown in FIG. 20.

An incision is created with a scalpel in the skin of the patient and a cannula 300 is positioned with a dilator 301 to form one or more passageways. Bone elements, for example, pins are translated through the passageways and are connected to vertebral tissue, including selected vertebrae, for example, the spinous process of thoracic vertebrae T11 and T12 (not shown), and a bone mount bridge 302, as shown in FIG. 20. In some embodiments, bridge 302 includes a minimally invasive surgical technique bridge. In some embodiments, bridge 302 is configured to connect surgical mount 12 with a robot R. In some embodiments, surgical mount 12 is alternatively mounted to an operating room table, navigational guidance NG, including a navigation reference frame to enable tracking, or is un-mounted.

The pins are connected to the vertebral tissue manually via a freehand surgical technique. A short mount coupler 304 is attached to bridge 302. The spine of the patient including vertebral surfaces described herein are registered with navigational guidance NG and a robot R, as shown in FIGS. 21 and 22. See, for example, similar surgical navigation and robotic systems, their components and use as described in U.S. Pat. No. 10,751,127, the entire contents of which being incorporated by reference herein. In some embodiments, a Schanz arm can be attached to the robot R. Registration includes implementing an O-arm for surgical planning and/or a C-arm for fluoroscopic registration. In some embodiments, vertebral levels are registered including thoracic vertebral levels T6 to T10.

Figures 23, 24, 25:
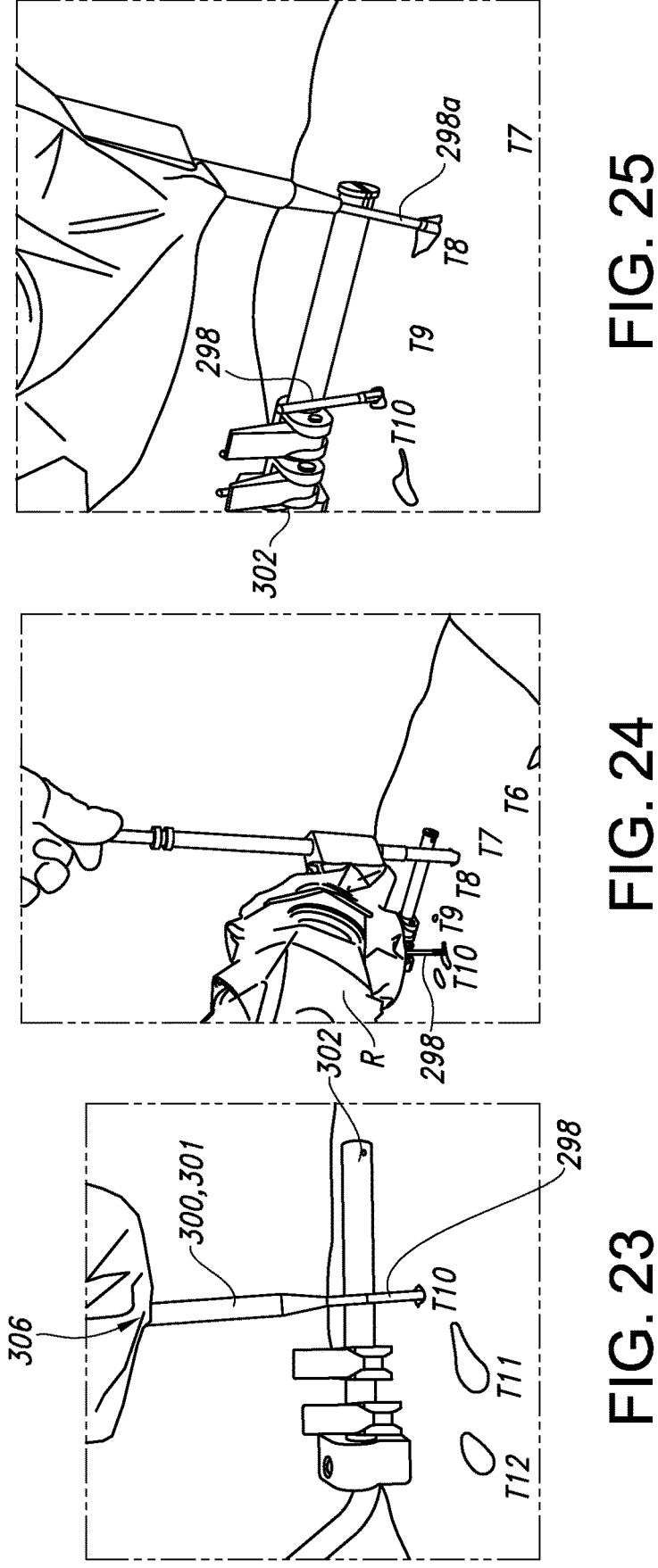
FIG. 23 is a side view of components of the system shown in FIG. 20.
FIG. 24 is a perspective view of components of the system shown in FIG. 20.
FIG. 25 is a perspective view of components of the system shown in FIG. 20.

An incision is created in the skin of the patient and cannula 300 is disposed with an end effector of robot R and aligned to position cannula 300 and dilator 301 at the incision site to form a passageway. A pin 298 is translated through the passageway and aligned at thoracic vertebra T10. A pin driver 306 is implemented via robot R to fix pin 298 into a pedicle of thoracic vertebra T10, as shown in FIGS. 22-23. A pin 298a, similar to pin 298, is fixed with thoracic vertebra T8, as shown in FIGS. 24-25.

Figure 26:
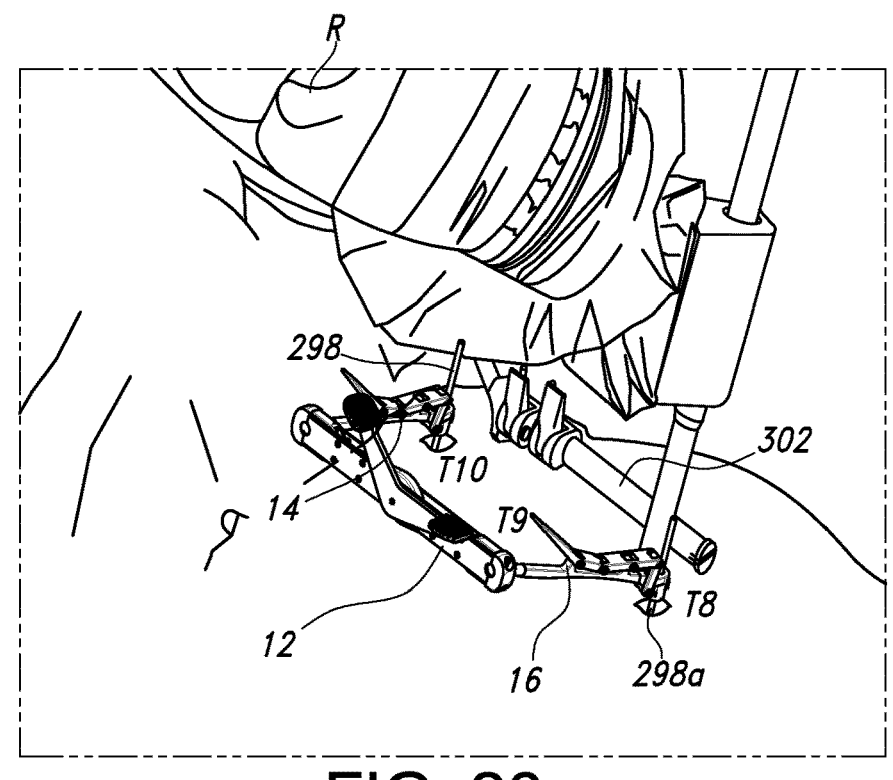
FIG. 26 is a perspective view of components of the system shown in FIG. 20.

Pin 298 is disposed with lock 96 to fix arm 14 with pin 298, as described herein. Lever 116 is depressed such that connected links 100, 102 translate pivot P2 from the over center orientation corresponding to the non-locking orientation to the over center orientation corresponding to the locking orientation. As links 100, 102 rotate to the over center orientation corresponding to the locking orientation, link 104 connected thereto rotates plate 106 such that surface 108 frictional engages pin 298 disposed with opening 134 to fix pin 298 with arm 14, as shown in FIG. 26 and described herein. Arm 16, similar to arm 14 is fixed with pin 298a. Pin 298a is stabilized via driver 306 while arm 16 of surgical mount 12 is fixed with pin 298a.

Upon desired positioning of arm 14 relative to arm 16 and/or vertebrae, handle 92 is depressed to move spheroidal joints 22, 34 into the locking orientation, as described herein, to fix relative position of arm 14 relative to arm 16 and/or vertebrae. Links 64, 66 rotate with plate 68 and elastically deform beyond an over-center position to move linkage 62 beyond a central axis. Links 64, 66 simultaneously draw end caps 28, 40 inwardly to eliminate the clearance between end caps 28, 40 and spherical parts 24, 36 such that end caps 28, 40 frictionally engage spherical parts 24, 36. In some embodiments, surgical mount 12 provides stability to thoracic vertebra T10, T8 and pins 298, 298a.

Figure 27:
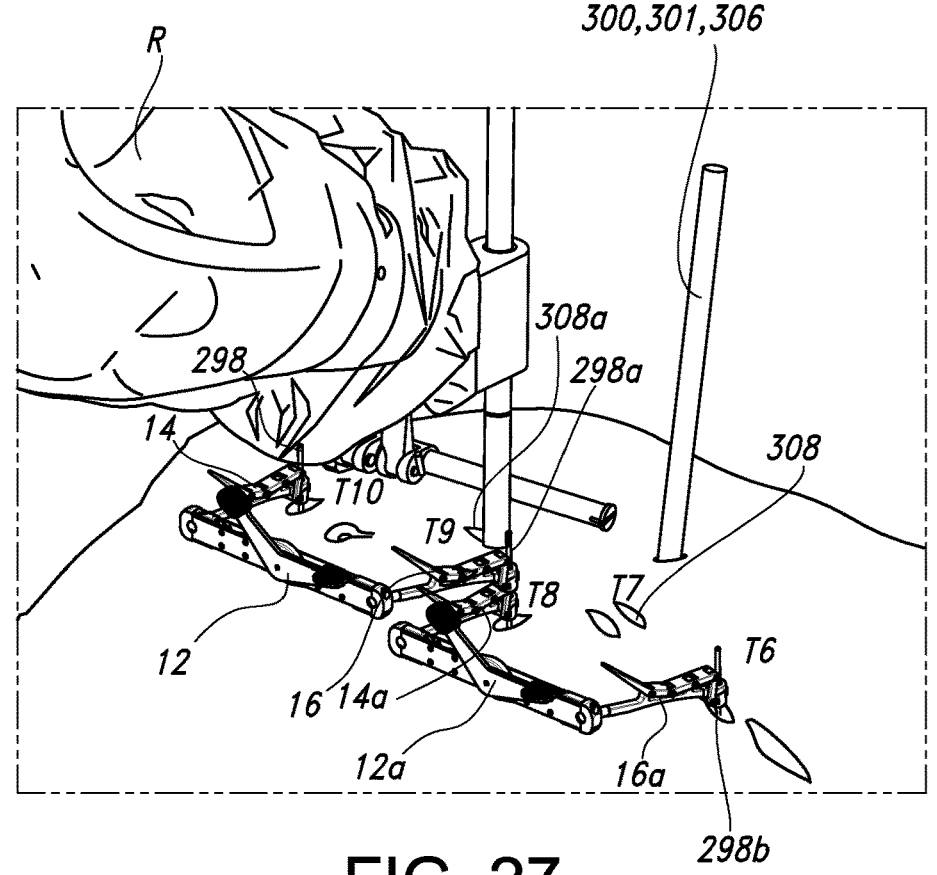
FIG. 27 is a perspective view of components of the system shown in FIG. 20.

A pin 298b, similar to pin 298, is fixed with thoracic vertebra T6, as shown in FIG. 27. Arms 14a, 16a of surgical mount 12a, similar to surgical mount 12 are connected to thoracic vertebrae T8 and T6 via pins 298a, 298b. An incision is created in the skin of the patient for a bone fastener, for example, a bone screw 308 such that cannula 300 is disposed with the end effector of robot R and aligned to position cannula 300 and dilator 301 at the incision site to form a passageway. Bone screw 308 is translated through the passageway and aligned at thoracic vertebra T7. A driver is implemented via robot R to fix bone screw 308 with a right side of thoracic vertebra T7, as shown in FIG. 27.

Figure 28:
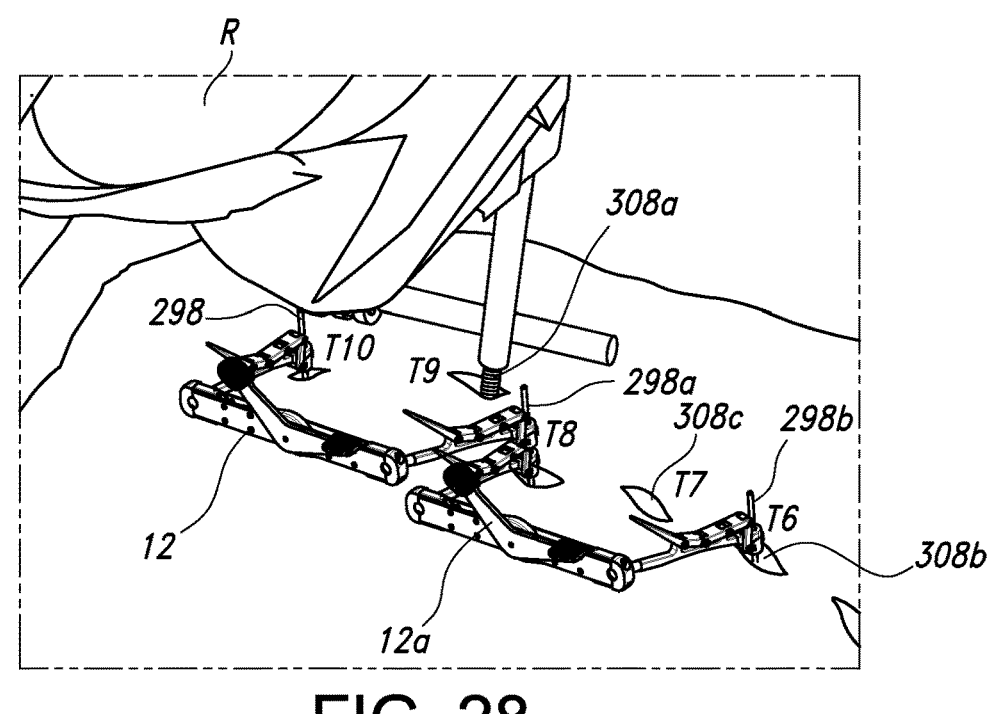
FIG. 28 is a perspective view of components of the system shown in FIG. 20.

In some embodiments, a bone screw 308a, similar to bone screw 308, is fixed with a right side of thoracic vertebra T9, as shown in FIGS. 27-28. A bone screw 308b, similar to bone screw 308, is fixed with a left side of thoracic vertebra T6, as shown in FIG. 28. A bone screw 308c, similar to bone screw 308, is fixed with a left side of thoracic vertebra T7, as shown in FIG. 28.

Figure 29:
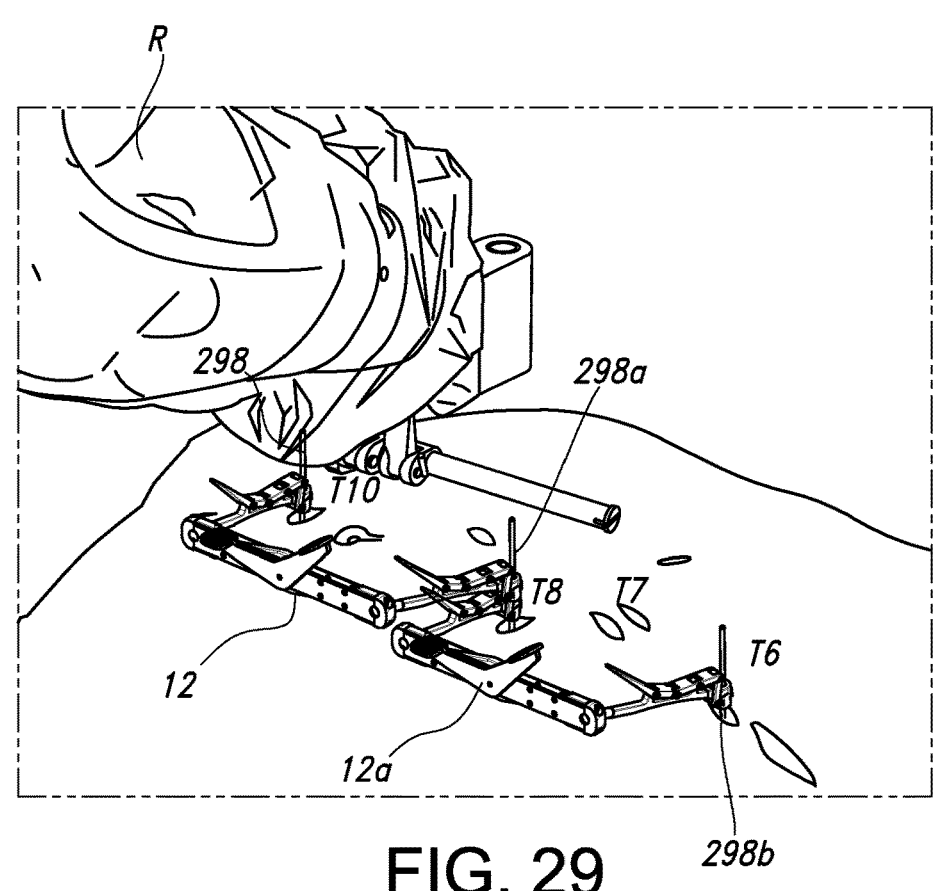
FIG. 29 is a perspective view of components of the system shown in FIG. 20.
Figure 30:
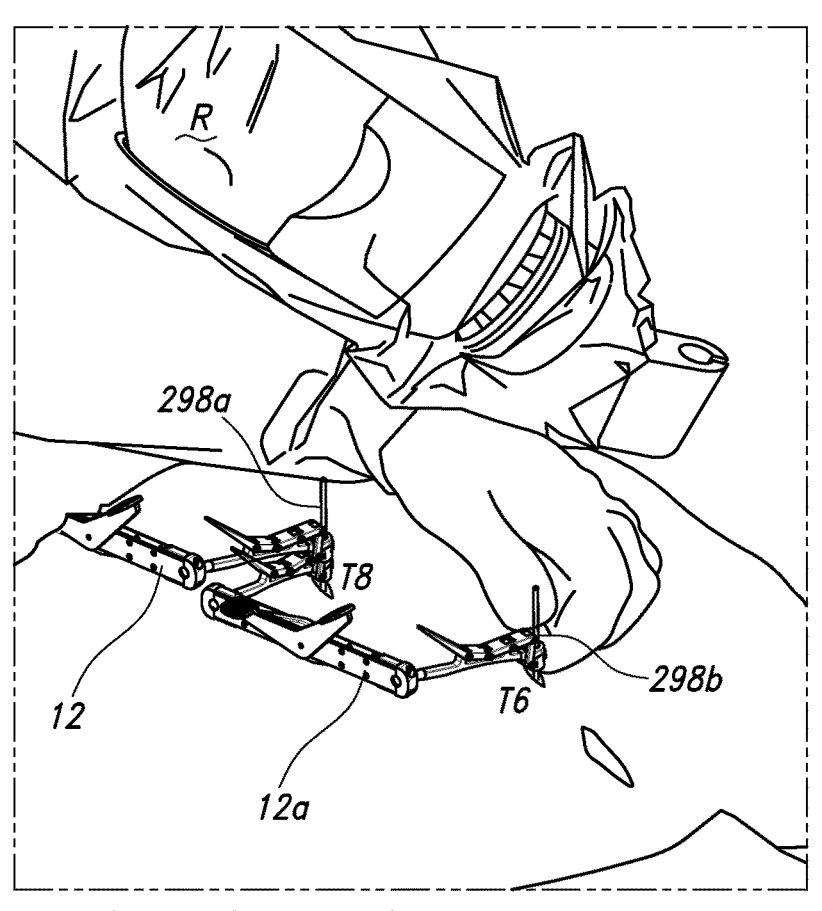
FIG. 30 is a perspective view of components of the system shown in FIG. 20.
Figure 31:
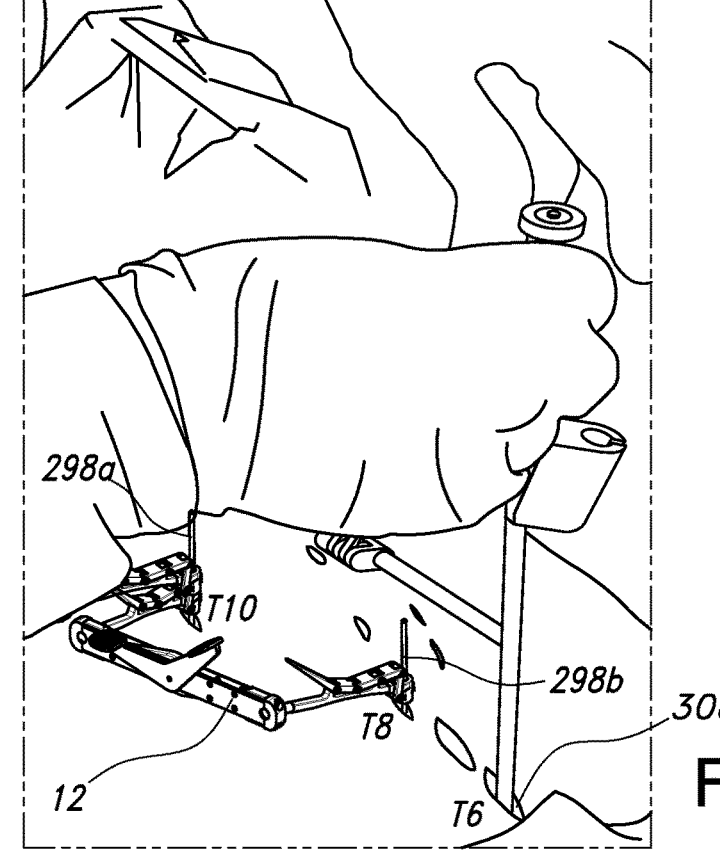
FIG. 31 is a perspective view of components of the system shown in FIG. 20.
Figure 32:
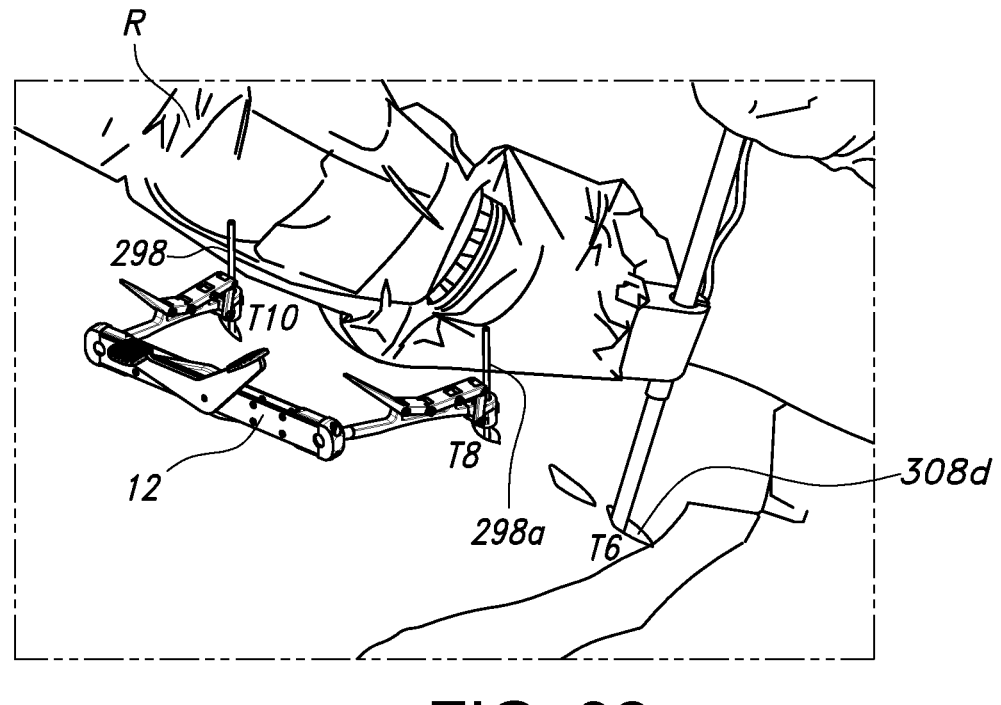
FIG. 32 is a perspective view of components of the system shown in FIG. 20.

To remove arms 14a, 16a from pins 298a, 298b, similar to arms 14, 16 described herein, levers 116a, 164a are engaged to dispose locks 96a, 146a in a non-locking orientation, such that arms 14a, 16a are released therefrom, as shown in FIGS. 29-30. Surgical mount 12a is removed from the surgical site. In some embodiments, pin 298b is removed and a bone screw 308d, similar to bone screw 308, is fixed with a right side of thoracic vertebra T6, as shown in FIGS. 31-32. Arms 14, 16 are disposed in a non-locking orientation for removal from pins 298, 298a, similar to that described herein. Surgical mount 12 is removed from the surgical site.

In some embodiments, components of surgical system 10 are re-registered. In some embodiments, a C-arm is employed to re-register. In some embodiments, the planned trajectories of the bone screws are compared to actual bone screw placement. Upon completion of the procedure, incision sites are closed. In some embodiments, one or more surgical mounts 12 may be employed during the surgical procedure.

Figures 33, 34:
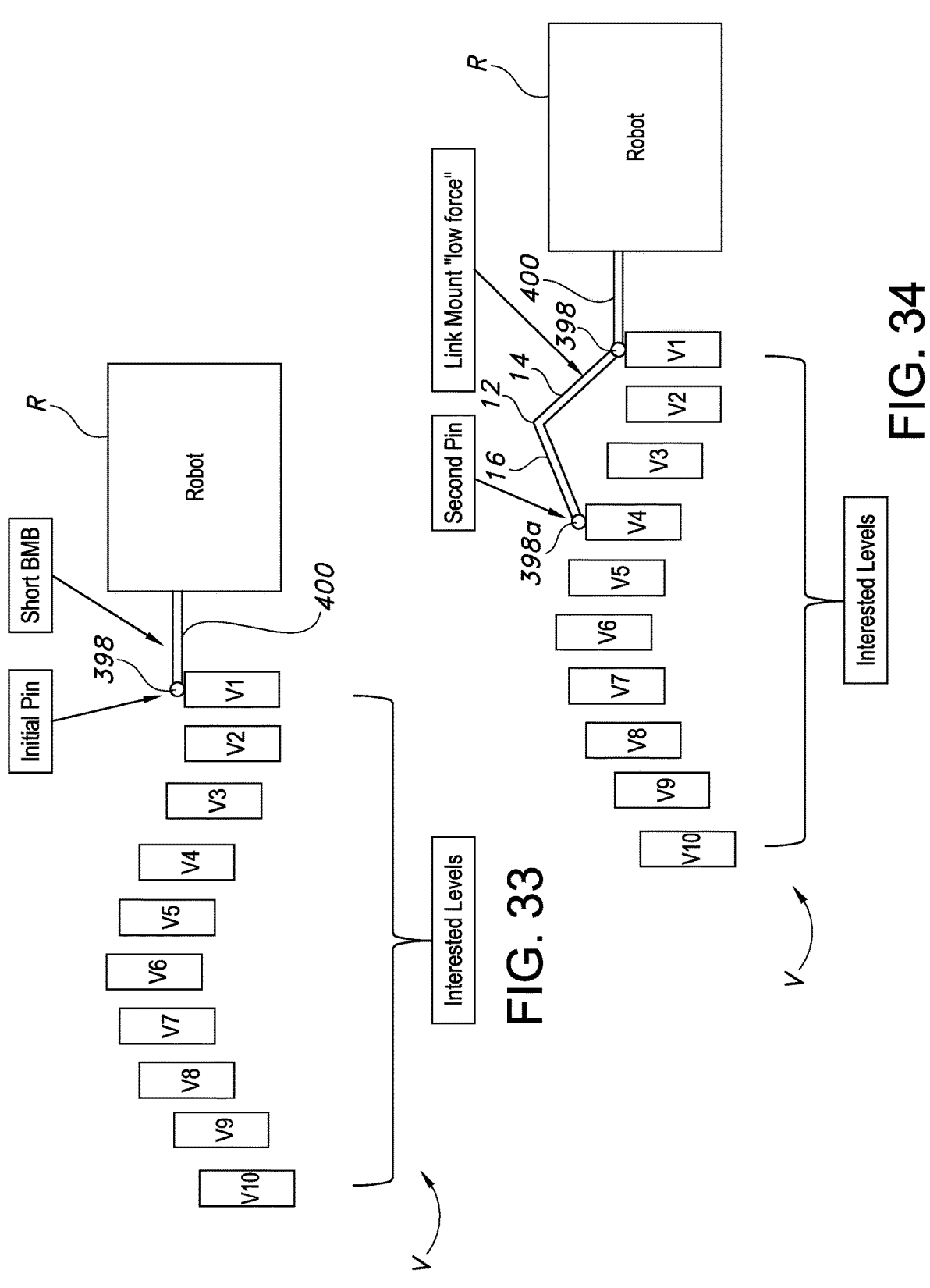
FIG. 33 is a perspective view of components of one embodiment of a surgical system in accordance with the principles of the present disclosure.
FIG. 34 is a perspective view of components of the system shown of FIG. 33.

In one embodiment, a method for treating a selected section of vertebrae V, similar to that described herein, as shown in FIGS. 33-40, includes a pin 398 being fixed with the lowest pedicle of vertebra V1, as shown in FIG. 33. Pin 398 is driven manually via a freehand surgical technique into V1. A bone mount bridge 400 is attached to pin 398. In some embodiments, a spinous process clamp (not shown) is attached to the bone mount bridge 400 and vertebra V1 prior to pin 398 attachment. Vertebrae V of the patient are registered with navigational guidance and a robot R, similar to that described herein.

An incision is created with the scalpel in the skin of the patient and the cannula is disposed with an end effector of robot R and aligned to position the cannula and the dilator at the incision site to form a passageway. A pin 398a is translated through the passageway and aligned at vertebra V4. A driver is implemented via robot R to fix pin 398a with vertebra V4, as shown in FIG. 34.

Arms 14, 16 similar to arm to pin fixation described herein, are fixed with pins 398, 398a. Upon desired positioning of arm 14 relative to arm 16 and/or vertebrae, handle 92 is depressed to move spheroidal joints 22, 34 into the locking orientation, as described herein, to fix relative position of arm 14 relative to arm 16 and/or vertebrae. In some embodiments, spinous process clamps (not shown) can be utilized as an alternative to pins 398, 398a to connect vertebrae together via surgical mount 12.

Figures 35, 36:
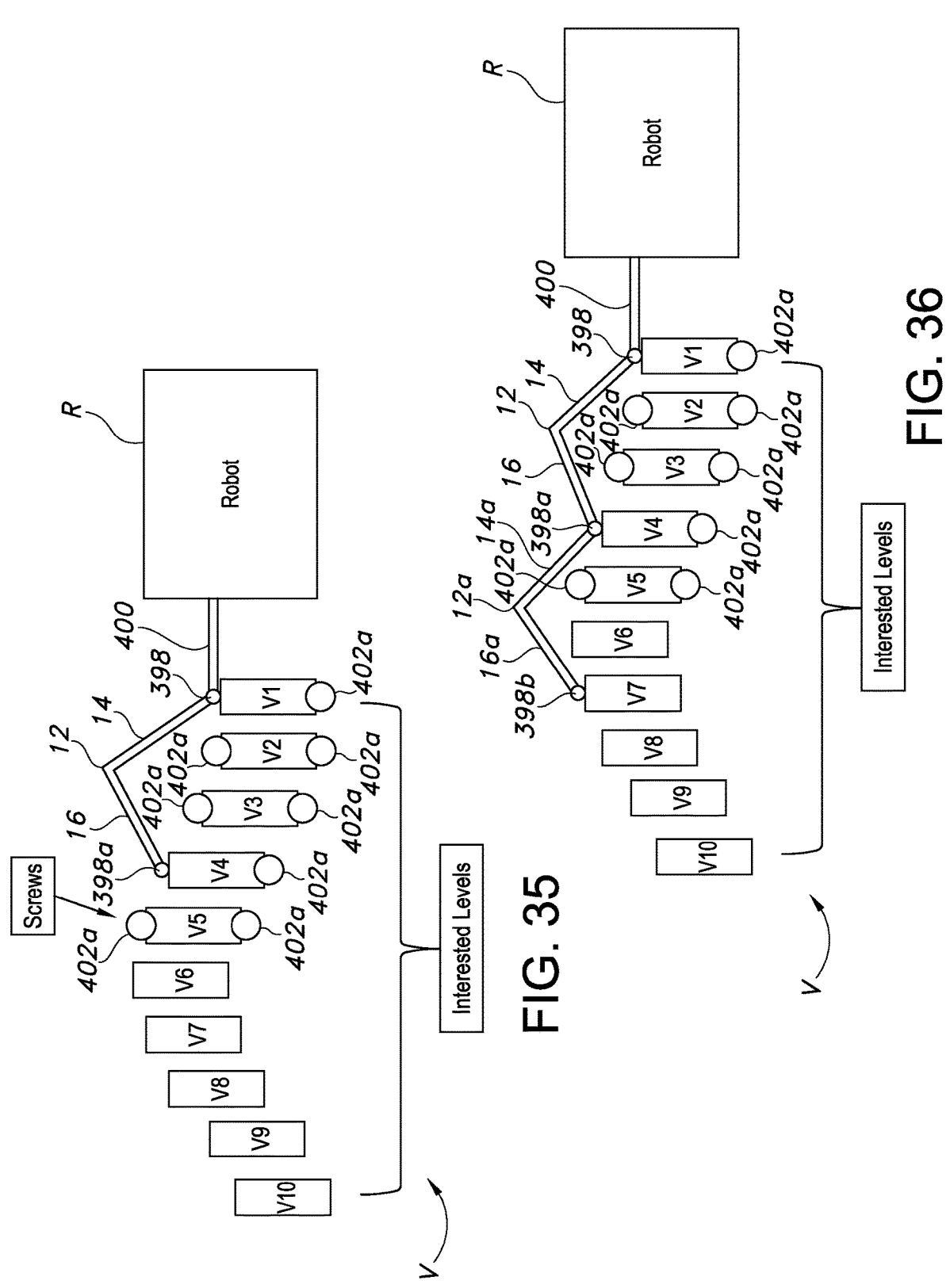
FIG. 35 is a perspective view of components of the system shown in FIG. 33.
FIG. 36 is a perspective view of components of the system shown in FIG. 33.
Figures 37, 38:
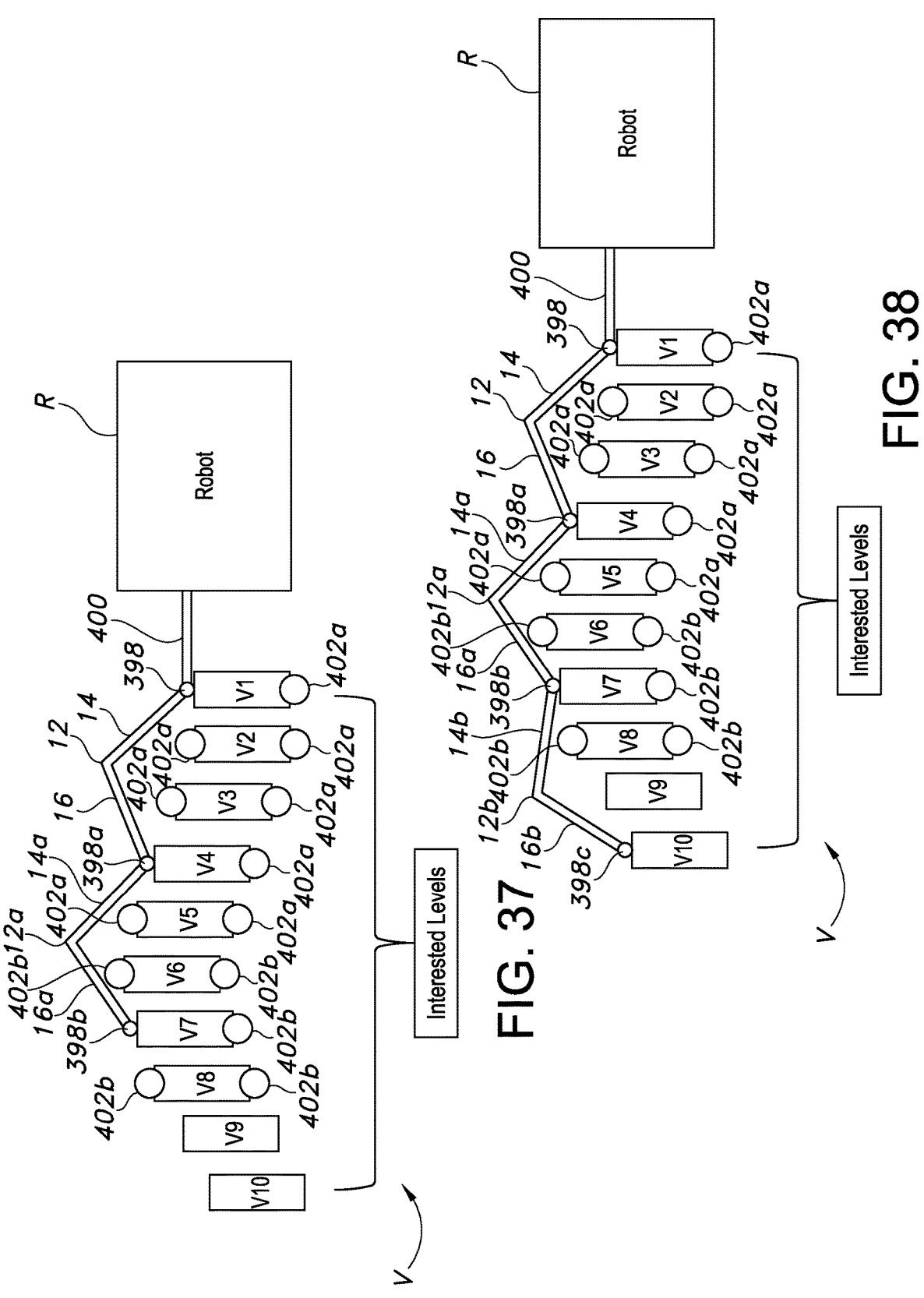
FIG. 37 is a perspective view of components of the system shown in FIG. 33.
FIG. 38 is a perspective view of components of the system shown in FIG. 33.
Figures 39, 40:
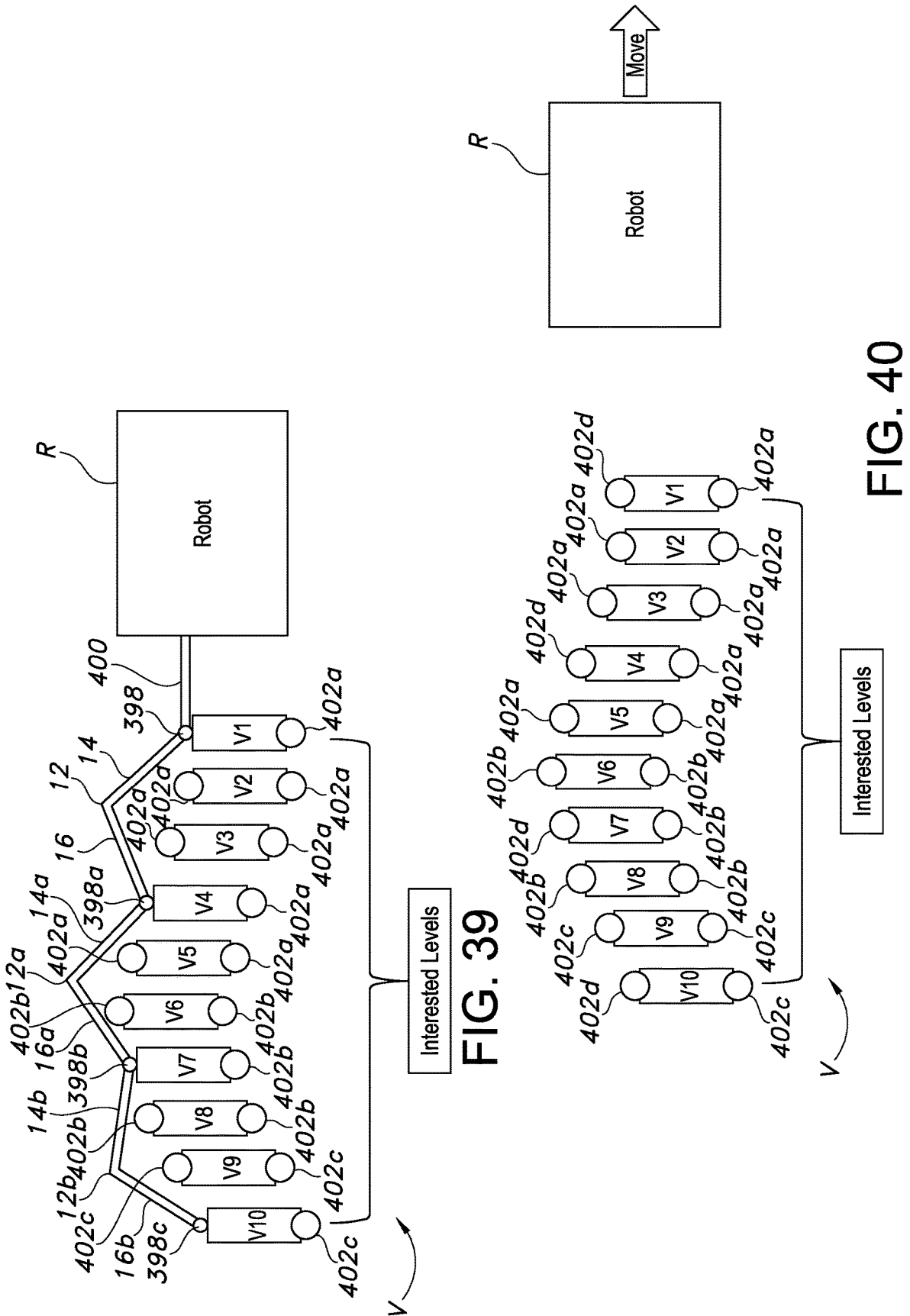
FIG. 39 is a perspective view of components of the system shown in FIG. 33.
FIG. 40 is a perspective view of components of the system shown in FIG. 33.

In some embodiments, bone screws 402a are translated through selected passageways and aligned between and above vertebrae V1-V5, as described herein. In some embodiments, the driver is implemented via robot R to fix bone screws 402a adjacent V1-V5, as shown in FIG. 35. For example, a pin 398b, similar to pin 398, is fixed with vertebra V7, as shown in FIG. 36. A surgical mount 12a is fixed with pins 398a, 398b via arms 14a, 16a, similar to the arm to pin fixation described herein. Bone screws 402b, similar to bone screws 402a, are positioned and fixed between and above pin 398b at vertebrae V6-V8, as shown in FIG. 37. A pin 398c, similar to pin 398, is fixed with vertebra V10, as shown in FIG. 38. A surgical mount 12b is fixed with pins 398b, 398c via arms 14b, 16b, similar to the arm to pin fixation described herein. Bone screws 402c, similar to bone screws 402a, are positioned and fixed between and below pin 398c at vertebrae V9-V10, as shown in FIG. 39.

To remove arms 14, 16 from pins 398, 398*a*, levers 116, 164 are engaged to dispose locks 96, 146 in a non-locking orientation, such that arms 14, 16 are released therefrom, similar to that described herein. Arms 14*a*, 16*a* are removed from pins 398*a*, 398*b* and arms 14*b*, 16*b* are removed from pins 398*b*, 398*c* in a similar manner to that described herein. Pins 398, 398*a*, 398*b*, 398*c* are removed from the surgical site via robot R. In some embodiments, bone screws 402*d*, similar to bone screws 402*a* are positioned and fixed into pin holes formed by pins 398, 398*a*, 398*b*, 398*c*.

One or more of the components of surgical system 10 can be made of radiolucent materials such as polymers. Radiopaque markers may be included for identification under x-ray, fluoroscopy, CT, or other imaging techniques. In some embodiments, the use of surgical navigation, microsurgical and image guided technologies, as described herein, may be employed to access, view and repair spinal deterioration or damage, with the aid of surgical system 10. In some embodiments, surgical system 10 may include implants and/or spinal constructs, which may include one or a plurality of plates, rods, connectors and/or bone fasteners for use with a single vertebral level or a plurality of vertebral levels.

In some embodiments, the surgical system of the present disclosure and related methods of use may be described by reference to the following numbered paragraphs:

A method for treating a spine, the method comprising the steps of: registering a plurality of vertebrae including at least a first vertebra and a second vertebra; fixing a first bone element with the first vertebra; fixing a second bone element with the second vertebra; engaging a first lock of a surgical instrument with the first bone element in a locking orientation, the surgical instrument including a first member having at least a portion of a first spheroidal joint and the first lock, the surgical instrument further including a second member including at least a portion of a second spheroidal joint and a second lock, and a linkage; engaging the second lock with the second bone element in a locking orientation; and simultaneously engaging the spheroidal joints to lock the second member relative to the first member.

The method for treating a spine of the preceding paragraph, wherein the first spheroidal joint includes a first spherical part and a first socket, the first socket being movable relative to the first spherical part in a non-locking orientation and fixable with the first spherical part in a locking orientation to lock the second member relative to the first member fixed with the first vertebrae.

The method for treating a spine of the preceding paragraph, wherein the step of fixing the second bone element with the second vertebra includes aligning the second bone element with the second vertebra via robotic guidance.

The method for treating a spine of the preceding paragraph, wherein the step of fixing the first bone element with the first vertebra includes aligning the first bone element with the first vertebra via robotic guidance.

The method for treating a spine of the preceding paragraph, further comprising the step of fixing a first bone fastener with a third vertebra disposed between the first vertebra and the second vertebra, fixing a third bone element with a fourth vertebra and fixing a second bone fastener with a fifth vertebra disposed between the fourth vertebra and the second vertebra.

The method for treating a spine of the preceding paragraph, wherein the step of fixing the third bone element with the fourth vertebra includes aligning the third bone element with the fourth vertebra via robotic guidance.

A method for treating a spine, the method comprising the steps of: registering a plurality of vertebrae including at least a first vertebra, a second vertebra, a third vertebra, a fourth vertebra, a fifth vertebra and a sixth vertebra; manually fixing a first bone pin with the first vertebra; fixing a second bone pin with the second vertebra via robotic guidance; engaging a first lock of a surgical instrument with the first bone pin in a locking orientation, the surgical instrument including a first arm having at least a portion of a first spheroidal joint and the first lock, the surgical instrument further including a second arm including at least a portion of a second spheroidal joint and a second lock, and a linkage; engaging the second lock with the second bone pin in a locking orientation; simultaneously engaging the spheroidal joints to lock the second arm relative to the first arm; and fixing a first bone fastener with a third vertebra disposed between the first vertebra and the second vertebra.

The method for treating a spine of the preceding paragraph, further comprising the steps of fixing a third bone element with the fourth vertebra and fixing a second bone fastener with the fifth vertebra disposed between the fourth vertebra and the third vertebra.

The method for treating a spine of the preceding paragraph, wherein the step of fixing the third bone element with the fourth vertebra includes aligning the third bone element with the fourth vertebra via robotic guidance.

The method for treating a spine of the preceding paragraph, wherein the step of fixing the second bone fastener with the fifth vertebra includes aligning the second bone fastener with the fifth vertebra via robotic guidance.

The method for treating a spine of the preceding paragraph, further comprising the steps of fixing a fourth bone element with the sixth vertebra and fixing a third bone fastener with the seventh vertebra disposed between the sixth vertebra and the fifth vertebra.

The method for treating a spine of the preceding paragrap, wherein the step of fixing the fourth bone element with the sixth vertebra includes aligning the fourth bone element with the sixth vertebra via robotic guidance.

A surgical instrument comprising: a first member including at least a portion of a first spheroidal joint and a first lock engageable with a first bone element fixed with a first vertebra; a second member including at least a portion of a second spheroidal joint and a second lock engageable with a second bone element fixed with a second vertebra; and a linkage being simultaneously engageable with the spheroidal joints to lock the second member relative to the first member fixed with the first vertebra.

A surgical instrument as recited in the preceding paragraph, wherein the first spheroidal joint includes a first spherical part and a first socket being movable relative to the first spherical part.

A surgical instrument as recited in the preceding paragraph, wherein the first socket is movable relative to the first spherical part in a non-locking orientation and fixable with the first spherical part in a locking orientation to lock the second member relative to the first member fixed with the first vertebra.

A surgical instrument as recited in the preceding paragraph, further comprising a frame supporting the first socket such that the first socket is translatable relative to the frame between the non-locking orientation and the locking orientation.

A surgical instrument as recited in the preceding paragraph, wherein the linkage includes a lever and a first arcuate link connected with the first spheroidal joint and a second arcuate link connected with the second spheroidal joint, the lever being rotatable between a non-locking orientation and a locking orientation to lock the second member relative to the first member fixed with the first vertebra.

A surgical instrument as recited in the preceding paragraph, wherein the lever is rotatable to the locking orientation such that the lever is disposed in an over center position to tension the link and fix the spheroidal joints.

A surgical instrument as recited in the preceding paragraph, wherein the first lock includes a plate having an inner surface defining an opening configured for disposal of the first bone element, the inner surface being frictionally engageable with the first bone element to fix the first member with the first bone element.

A surgical instrument as recited in the preceding paragraph, wherein the first lock includes a plurality of links connected with the plate to move the plate between a non-locking orientation and a locking orientation such that the inner surface is frictionally engaged with the first bone element to fix the first member with the first bone element.

A surgical instrument comprising: a first member including at least a portion of a first spheroidal joint and a first lock engageable with a first bone element fixed with a first vertebral surface; a second member including at least a portion of a second spheroidal joint and a second lock engageable with a second bone element fixed with a second vertebral surface; and a linkage being simultaneously engageable with the spheroidal joints to lock the second member relative to the first member fixed with the first vertebral surface.

A surgical instrument as recited in the preceding paragraph, wherein the first spheroidal joint includes a first spherical part and a first socket being movable relative to the first spherical part.

A surgical instrument as recited in the preceding paragraph, wherein the first socket is movable relative to the first spherical part in a non-locking orientation and fixable with the first spherical part in a locking orientation to lock the second member relative to the first member fixed with the first vertebral surface.

A surgical instrument as recited in any of the preceding paragraphs, further comprising a frame supporting the first socket such that the first socket is linearly translatable relative to the frame between the non-locking orientation and the locking orientation.

A surgical instrument as recited in any of the three preceding paragraphs, wherein the linkage includes a lever and a first arcuate link connected with the first spheroidal joint and a second arcuate link connected with the second spheroidal joint, the lever being rotatable between a non-locking orientation and a locking orientation to lock the second member relative to the first member fixed with the first vertebral surface.

A surgical instrument as recited in the preceding paragraph, wherein the lever is rotatable to the locking orientation such that the lever is disposed in an over center position to tension the link and fix the spheroidal joints.

A surgical instrument as recited in any of the five preceding paragraphs, wherein the first lock includes a plate having an inner surface defining an opening configured for disposal of the first bone element, the inner surface being frictionally engageable with the first bone element to fix the first member with the first bone element.

A surgical instrument as recited in the preceding paragraph, wherein the first lock includes a plurality of links connected with the plate to move the plate between a non-locking orientation and a locking orientation such that the inner surface is frictionally engaged with the first bone element to fix the first member with the first bone element.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first member including at least a portion of a first spheroidal joint and a first lock engageable with a first bone element fixed with a first vertebra;
a second member including at least a portion of a second spheroidal joint and a second lock engageable with a second bone element fixed with a second vertebra; and
a linkage being simultaneously engageable with the spheroidal joints to lock the second member relative to the first member,
wherein the linkage includes a lever and a first arcuate link connected with the first spheroidal joint and a second arcuate link connected with the second spheroidal joint, the lever being rotatable between a non-locking orientation and a locking orientation to lock the second member relative to the first member,
wherein the first lock includes a plate having an inner surface defining an opening configured for disposal of the first bone element, the inner surface being frictionally engageable with the first bone element to fix the first member with the first bone element,
wherein the first spheroidal joint includes a first spherical part and a first socket being movable relative to the first spherical part,
wherein the first socket is movable relative to the first spherical part in a non-locking orientation and fixable with the first spherical part in a locking orientation to lock the second member relative to the first member, and
wherein the surgical instrument includes a frame supporting the first socket such that the first socket is translatable relative to the frame between the non-locking orientation and the locking orientation.

2. A surgical instrument as recited in claim 1, wherein the lever is rotatable such that the lever is disposed in an over center position to tension the links and fix the spheroidal joints.

3. A surgical instrument as recited in claim 1, wherein the first lock includes a plurality of links connected with the plate to move the plate between a non-locking orientation and a locking orientation such that the inner surface is frictionally engaged with the first bone element to fix the first member with the first bone element.

4. A surgical instrument comprising:
a first member including at least a portion of a first spheroidal joint and a first lock engageable with a first bone element fixed with a first vertebra;
a second member including at least a portion of a second spheroidal joint and a second lock engageable with a second bone element fixed with a second vertebra;
a linkage being simultaneously engageable with the spheroidal joints to lock the second member relative to the first member,
wherein the first spheroidal joint includes a first spherical part and a first socket being movable relative to the first spherical part, wherein the first socket is movable relative to the first spherical part in a non-locking orientation and fixable with the first spherical part in a locking orientation to lock the second member relative to the first member, wherein the surgical instrument includes a frame supporting the first socket such that the first socket is translatable relative to the frame between the non-locking orientation and the locking orientation, and wherein the first lock includes a plate having an inner surface defining an opening configured for disposal of the first bone element, the inner surface being frictionally engageable with the first bone element to fix the first member with the first bone element.

5. A surgical instrument as recited in claim 4, wherein the first lock includes a plurality of links connected with the plate to move the plate between a non-locking orientation and a locking orientation such that the inner surface is frictionally engaged with the first bone element to fix the first member with the first bone element.

6. A surgical instrument comprising:

a first member including a spherical part of a first spheroidal joint;

a second member including a spherical part of a second spheroidal joint;

a linkage comprising a frame, a first plate and a second plate;

a first end cap coupled to a first end of the frame; and a second end cap coupled to a second end of the frame, wherein a surface of first end cap and a surface of the first plate define a socket of the first spheroidal joint, wherein a surface of the second end cap and a surface of the second plate define a socket of the second spheroidal joint, wherein the spherical part of the first spheroidal joint is disposed in the socket of the first spheroidal joint and the spherical part of the second spheroidal joint is disposed in the socket of the second spheroidal joint, wherein the plates are movable relative to the end caps to move the plates between a non-locking orientation in which the members are movable relative to the end caps and a locking orientation in which the spherical parts are in fixation with the surfaces of the end caps to fix the members relative to the end caps, wherein the linkage includes a lever that is rotatable relative to the frame and the end caps to move the plates between the non-locking orientation and the locking orientation, and wherein the lever is positioned between the sockets.

7. A surgical instrument as recited in claim 6, further comprising:

a first link coupled to a first end of the lever and the first plate; and a second link coupled to a second end of the lever and the second plate.

8. A surgical instrument as recited in claim 6, wherein the frame includes a first rail and a second rail, the lever being positioned between the rails.

9. A surgical instrument as recited in claim 6, wherein the frame includes a first rail and a second rail, the plates being positioned between the rails.

10. A surgical instrument as recited in claim 9, wherein the rails are permanently fixed relative to one another.

11. A surgical instrument as recited in claim 6, wherein the spherical parts are not in fixation with the surfaces of the end caps when the plates are in the non-locking orientation.

12. A surgical instrument as recited in claim 6, wherein the first member includes a first lock engageable with a first bone element fixed with a first vertebra and the second member includes a second lock engageable with a second bone element fixed with a second vertebra.

13. A surgical instrument as recited in claim 12, wherein the first lock includes a first arm that defines a first channel, the first lock including a first part and a first linkage that is connected to the first part, the first linkage being moveable relative to the first arm between a first orientation in which a passageway of the first part is coaxial with the first channel and a second orientation in which the passageway is offset from the first channel.

14. A surgical instrument as recited in claim 13, wherein the second lock includes a second arm that defines a second channel, the second lock including a second part and a second linkage that is connected to the second part, the second linkage being moveable relative to the second arm between a first orientation in which a passageway of the second part is coaxial with the second channel and a second orientation in which the passageway of the second part is offset from the second channel.

15. A surgical instrument as recited in claim 13, wherein the first part is positioned between ends of the first channel when the first linkage is in the first orientation and the second orientation.

* * * * *